(12) United States Patent
Mihara et al.

(10) Patent No.: US 8,252,512 B2
(45) Date of Patent: Aug. 28, 2012

(54) EPOXY COMPOUND, ALKALI-DEVELOPABLE RESIN COMPOSITION, AND ALKALI-DEVELOPABLE PHOTOSENSITIVE RESIN COMPOSITION

(75) Inventors: Taiki Mihara, Tokyo (JP); Kiyoshi Murata, Tokyo (JP); Koichi Kimijima, Tokyo (JP)

(73) Assignee: Adeka Corporation, Tokyo (JP)

( * ) Notice: Subject to any disclaimer, the term of this patent is extended or adjusted under 35 U.S.C. 154(b) by 351 days.

(21) Appl. No.: 12/528,176

(22) PCT Filed: Apr. 28, 2008

(86) PCT No.: PCT/JP2008/058210
§ 371 (c)(1),
(2), (4) Date: Aug. 21, 2009

(87) PCT Pub. No.: WO2008/139924
PCT Pub. Date: Nov. 20, 2008

(65) Prior Publication Data
US 2010/0015551 A1    Jan. 21, 2010

(30) Foreign Application Priority Data
May 9, 2007    (JP) .................................. 2007-124550

(51) Int. Cl.
*C07D 3/24*    (2006.01)
*C08G 59/16*    (2006.01)
*G03F 7/028*    (2006.01)
(52) U.S. Cl. .................. 430/285.1; 430/280.1; 522/100; 528/87
(58) Field of Classification Search .......................... None
See application file for complete search history.

(56) References Cited

U.S. PATENT DOCUMENTS

| 3,708,296 | A | * | 1/1973 | Schlesinger | .................. | 430/176 |
| 3,977,878 | A | * | 8/1976 | Roteman | .................... | 430/275.1 |
| 5,362,597 | A | * | 11/1994 | Sano et al. | .................... | 430/191 |
| 2006/0204891 | A1 | * | 9/2006 | Hatakeyama | .............. | 430/270.1 |

FOREIGN PATENT DOCUMENTS

| EP | 1 548 043 | 6/2005 |
| JP | 2000-235261 | 8/2000 |
| JP | 2000-355621 | 12/2000 |
| WO | 2006/121062 | 11/2006 |
| WO | 2007/032326 | 3/2007 |
| WO | 2007/049665 | 5/2007 |

OTHER PUBLICATIONS

Hara, Osamu, "Curing Agents for Epoxy Resin", ThreeBOnd Technical News, 32, issued Dec. 20, 1990, 10 pages.*
European Search Report—PCT/JP2008/058210—Jan. 4, 2011.
International Search Report—PCT/JP2008/058210—Jul. 22, 2008.
Morgan, P.W.—Aromatic Polyesters with Large Cross-Planar Substituents, Macromolecules, 1970, vol. 3, No. 5, p. 536-544.

* cited by examiner

*Primary Examiner* — Cynthia Hamilton
(74) *Attorney, Agent, or Firm* — Young & Thompson

(57) ABSTRACT

An novel epoxy compound is represented by the general formula (I) and has a benzo- or naphtho-cycloalkane skeleton:

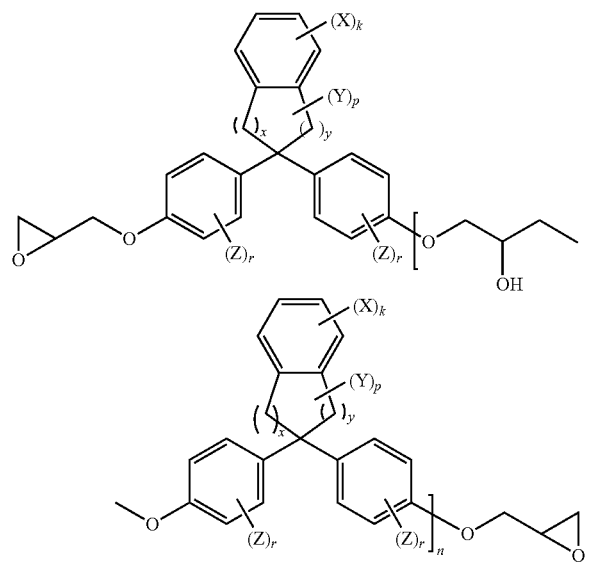

X, Y, and Z each independently represent an alkyl group having 1-10 carbon atoms and optionally substituted with a halogen atom, an aryl group having 6-20 carbon atoms and optionally substituted with a halogen atom, an arylalkyl group having 7-20 carbon atoms and optionally substituted with a halogen atom, a heterocyclic group having 2-20 carbon atoms and optionally substituted with a halogen atom, or a halogen atom; k represents a number of 0-4; p represents a number of 0-8; r represents a number of 0-4; n represents 0-10; x represents a number of 0-4; y represents a number of 0-4; a sum of x and y is 2-4; and an optical isomer that exists when n is not 0 may be of any type.

9 Claims, No Drawings

EPOXY COMPOUND, ALKALI-DEVELOPABLE RESIN COMPOSITION, AND ALKALI-DEVELOPABLE PHOTOSENSITIVE RESIN COMPOSITION

TECHNICAL FIELD

The present invention relates to a novel epoxy compound having a benzo- or naphtho-cycloalkane skeleton, a specific compound obtained by providing an ethylenically unsaturated bond to the epoxy compound, an alkali-developable resin composition containing a compound obtained by esterification of the above compound and a polybasic acid anhydride, and an alkali-developable photosensitive resin composition containing a photopolymerization initiator in the above alkali-developable resin composition.

BACKGROUND ART

An alkali-developable photosensitive resin composition contains an alkali-developable resin composition containing a compound having an ethylenically unsaturated bond, and a photopolymerization initiator. Such an alkali-developable photosensitive resin composition can be cured by polymerization on being irradiated with ultraviolet light or an electron beam, and is thus applicable to photo-curing inks, photosensitive printing plates, printed wiring boards, various kinds of photoresists, and so forth. Recent developments in downsizing and function enhancement of electronic devices have boosted the demand for alkali-developable photosensitive resin compositions that allow fine and precise patterning.

Patent Document 1 listed below proposes a photosensitive resin composition containing a prepolymer having an ethylenically unsaturated bond as one type of alkali-developable resin composition or alkali-developable photosensitive resin composition. Further, Patent Document 2 listed below proposes a photosensitive resin composition containing a polycarboxylic acid resin having an unsaturated group. However, these known alkali-developable photosensitive resin compositions are insufficient in terms of sensitivity, resolution, and adhesion, thus rendering formation of proper patterns or fine patterns difficult. Therefore, there is a demand for an alkali-developable photosensitive resin composition having good sensitivity and adhesion and capable of forming fine patterns with great precision.

Non-Patent Document 1 listed below discloses a bisphenol compound having a benzocycloalkane skeleton. However, the document neither discloses nor suggests an example in which the bisphenol compound is derived into an epoxy compound.

Patent Document 1: Japanese Patent Laid Open JP-A-2000-235261
Patent Document 2: Japanese Patent Laid Open JP-A-2000-355621
Non-Patent Document 1: Macromolecules, 3, 536 (1970)

DISCLOSURE OF THE INVENTION

Problem to be Solved by Invention

One problem to be solved lies in the fact that there has never been available an alkali-developable resin composition or an alkali-developable photosensitive resin composition having good sensitivity and adhesion and capable of forming proper and fine patterns, as discussed above.

Accordingly, an object of the present invention is to provide a useful and novel compound that serves as a material for an alkali-developable resin composition and an alkali-developable photosensitive resin composition having good sensitivity and adhesion and capable of forming fine patterns with great precision, and to provide an alkali-developable resin composition and an alkali-developable photosensitive resin composition employing the above compound.

Means for Solving the Problem

After diligent research, Inventors have found that a novel epoxy compound having a benzo- or naphtho-cycloalkane skeleton can achieve the above object.

The present invention has been achieved based on this finding, and provides an epoxy compound (A) represented by following general formula (I):

[Formula 1]

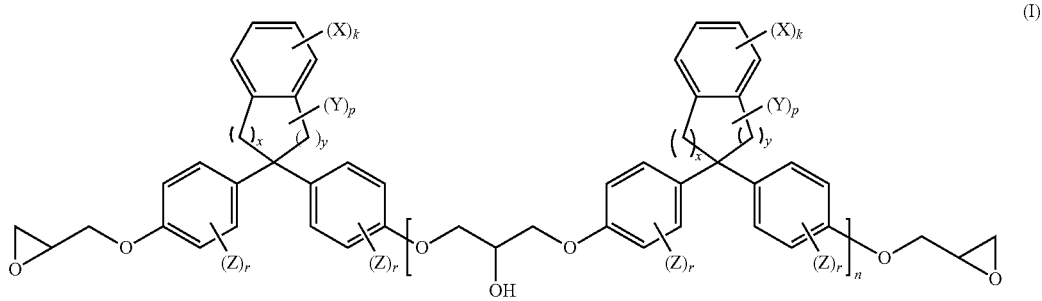

(I)

wherein, X, Y, and Z each independently represent an alkyl having 1 to 10 carbon atoms and optionally substituted with a halogen atom, an aryl group having 6 to 20 carbon atoms and optionally substituted with a halogen atom, an arylalkyl group having 7 to 20 carbon atoms and optionally substituted with a halogen atom, a heterocyclic group having 2 to 20 carbon atoms and optionally substituted with a halogen atom, or a halogen atom; a methylene group in the alkyl group, the aryl group, or the arylalkyl group may be interrupted by an unsaturated bond, —O—, or —S—; X may form a ring with the other X; the ring may be an aromatic ring; k represents a number of 0 to 4; p represents a number of 0 to 8; r represents a number of 0 to 4; n represents 0 to 10; x represents a number of 0 to 4; y represents a number of 0 to 4; a sum of x and y is 2 to 4; and an optical isomer that exists when n is not 0 may be of any type.

The present invention further provides an epoxy adduct (W) having a structure formed by adding an unsaturated monobasic acid (B) to the epoxy compound (A).

The present invention further provides an epoxy resin composition comprising the epoxy compound (A) and a curing agent.

The present invention further provides an alkali-developable resin composition comprising a photopolymerizable unsaturated compound (X) having a structure of a reaction product obtained by esterification between the epoxy adduct (W) and a polybasic acid anhydride (C).

The present invention further provides an alkali-developable resin composition comprising a photopolymerizable unsaturated compound (Y) having a structure of a reaction product obtained by further adding an epoxy compound (D) to the photopolymerizable unsaturated compound (X).

The present invention further provides an alkali-developable resin composition comprising a photopolymerizable unsaturated compound (Z) having a structure of a reaction product obtained by further esterifying a polybasic acid anhydride (E) to the photopolymerizable unsaturated compound (Y).

The present invention further provides an alkali-developable photosensitive resin composition comprising the alkali-developable resin composition(s) and a photopolymerization initiator (F).

The present invention further provides an alkali-developable, colored photosensitive resin composition comprising the alkali-developable photosensitive resin composition and a colorant (G).

BEST MODE FOR CARRYING OUT THE INVENTION

The following describes in detail an epoxy compound (A), an epoxy adduct (W), an epoxy resin composition, an alkali-developable resin composition, an alkali-developable photosensitive resin composition, and an alkali-developable, colored photosensitive resin composition of the present invention according to preferred embodiments thereof.

In the general formula (I) of the epoxy compound (A) of the present invention, examples of the alkyl group represented by X, Y, and Z having 1 to 10 carbon atoms and optionally substituted with a halogen atom include linear, branched, and cyclic alkyl groups, such as methyl, ethyl, propyl, isopropyl, butyl, s-butyl, t-butyl, isobutyl, amyl, isoamyl, t-amyl, hexyl, heptyl, isoheptyl, t-heptyl, n-octyl, isooctyl, t-octyl, 2-ethylhexyl, n-nonyl, n-decyl, trifluoromethyl, difluoromethyl, monofluoromethyl, pentafluoroethyl, tetrafluoroethyl, trifluoroethyl, difluoroethyl, heptafluoropropyl, hexafluoropropyl, pentafluoropropyl, tetrafluoropropyl, trifluoropropyl, perfluorobutyl, methoxy, methoxyethoxy, methoxyethoxyethoxy, methylthio, ethoxy, vinyloxy, propoxy, isopropoxy, butoxy, isobutoxy, t-butoxy, t-butoxycarbonylmethoxy, pentyloxy, isopentyloxy, t-pentyloxy, neopentyloxy, hexyloxy, cyclohexyloxy, isohexyloxy, heptyloxy, octyloxy, 2-ethylhexyloxy, nonyloxy, decyloxy, cyclopropyl, cyclobutyl, cyclopentyl, cyclohexyl, cycloheptyl, cyclooctyl, cyclononyl, and cyclodecyl. Examples of the aryl group having 6 to 20 carbon atoms and optionally substituted with a halogen atom include phenyl, 1-naphthyl, 2-naphthyl, 1-anthryl, 1-phenanthryl, o-tolyl, m-tolyl, p-tolyl, 3-fluorenyl, 9-fluorenyl, 1-tetrahydronaphthyl, 2-tetrahydronaphthyl, 1-acenaphthenyl, 1-indanyl, 2-indanyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t-amylphenyl, cyclohexylphenyl, biphenyl, 2,4,5-trimethylphenyl, 4-chlorophenyl, 3,4-dichlorophenyl, 4-trichlorophenyl, 4-trifluorophenyl, perfluorophenyl, phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, 1-naphthoxy, 2-naphthoxy, 1-anthryloxy, 1-phenanthryloxy, o-tolyloxy, m-tolyloxy, p-tolyloxy, 9-fluorenyloxy, 1-tetrahydronaphthoxy, 2-tetrahydronaphthoxy, 1-acenaphthenyloxy, 1-indanyloxy, and 2-indanyloxy. Examples of the arylalkyl group having 7 to 20 carbon atoms and optionally substituted with a halogen atom include benzyl, phenethyl, 2-phenylpropyl, diphenylmethyl, triphenylmethyl, styryl, cinnamyl, 4-chlorophenylmethyl, benzyloxy, 1-naphthylmethoxy, 2-naphthylmethoxy, and 1-anthrylmethoxy. Examples of the heterocyclic group having 2 to 20 carbon atoms and optionally substituted with a halogen atom include pyrrolyl, pyridyl, pyrimidyl, pyridazyl, piperazyl, piperidyl, pyranyl, pyrazolyl, triazyl, pyrrolidyl, quinolyl, isoquinolyl, imidazolyl, benzoimidazolyl, triazolyl, furyl, furanyl, benzofuranyl, thienyl, thiophenyl, benzothiophenyl, thiadiazolyl, thiazolyl, benzothiazolyl, oxazolyl, benzooxazolyl, isothiazolyl, isooxazolyl, indolyl, julolidyl, morpholinyl, thiomorpholinyl, 2-pyrrolidinon-1-yl, 2-piperidon-1-yl, 2,4-dioxyimidazolidin-3-yl, and 2,4-dioxyoxazolidin-3-yl. The halogen atom may be fluorine, chlorine, bromine, and iodine. Examples of the ring structure that may be formed by the Xs include five- to seven-membered rings, such as a cyclopentane ring, a cyclohexane ring, a cyclopentene ring, a benzene ring, a piperidine ring, a morpholine ring, a lactone ring, and a lactam ring, and fused rings, such as a naphthalene ring, an anthracene ring, a fluorene ring, an acenaphthene ring, an indan ring, and a tetralin ring.

A methylene group in above-described alkyl group, aryl group, or arylalkyl group represented by X, Y, and Z may be interrupted by an unsaturated bond, —O—, or —S—. The position for substitution by the halogen group as well as the position for interruption by —O— or —S— may be set freely, and —O— or —S— may be directly bonded to the ring.

In the epoxy compound (A) of the present invention, optical isomers may exist in case n is not 0. Any isomer is adoptable, and compounds described hereinbelow are not to be limited to a specific optical isomer.

Examples of the epoxy compound (A) of the present invention include compounds shown in [Formula 2] to [Formula 9] below, but are not to be limited thereto. Note that in the following formulae, n represents a number of 0 to 10.

[Formula 2]
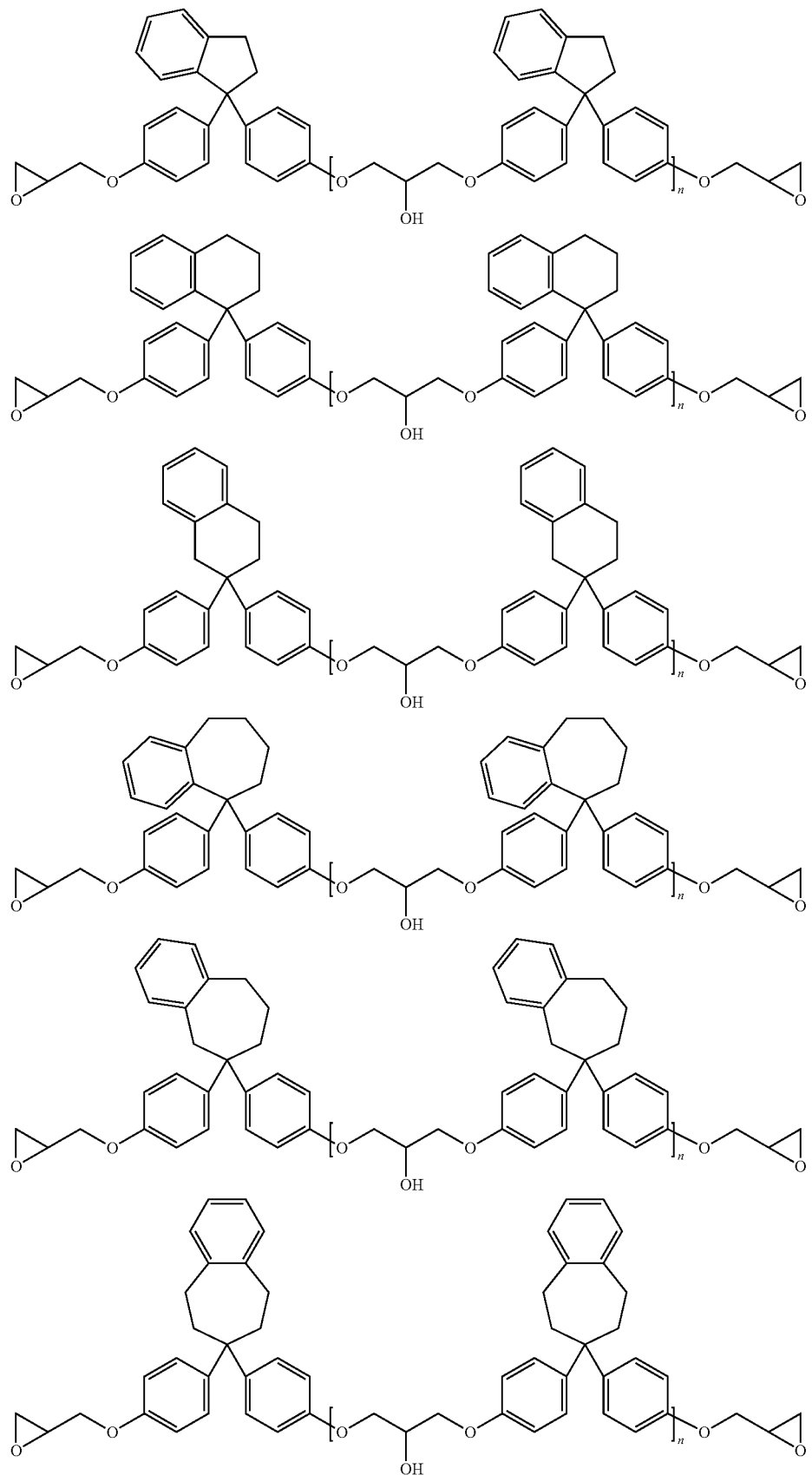

[Formula 3]
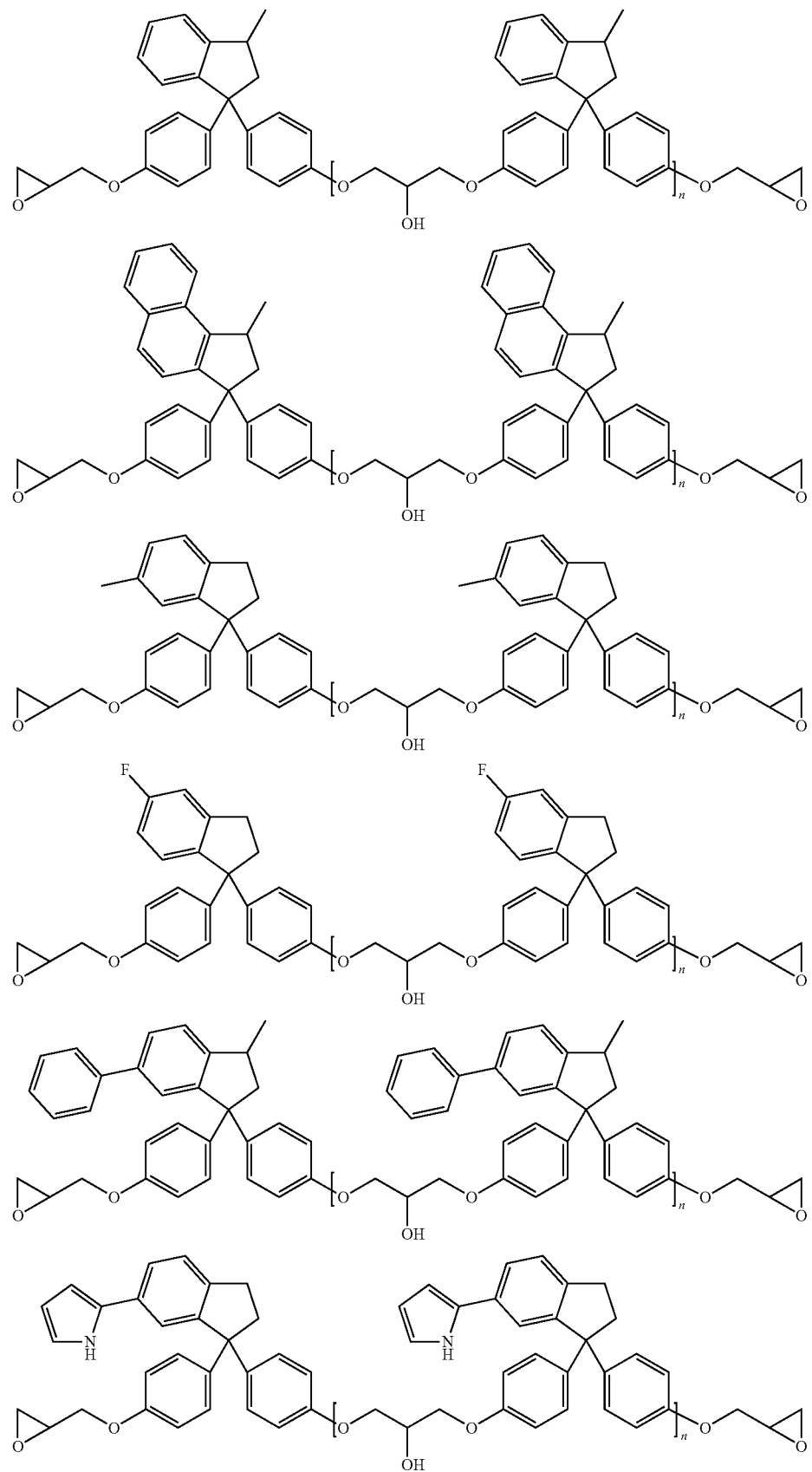

[Formula 4]
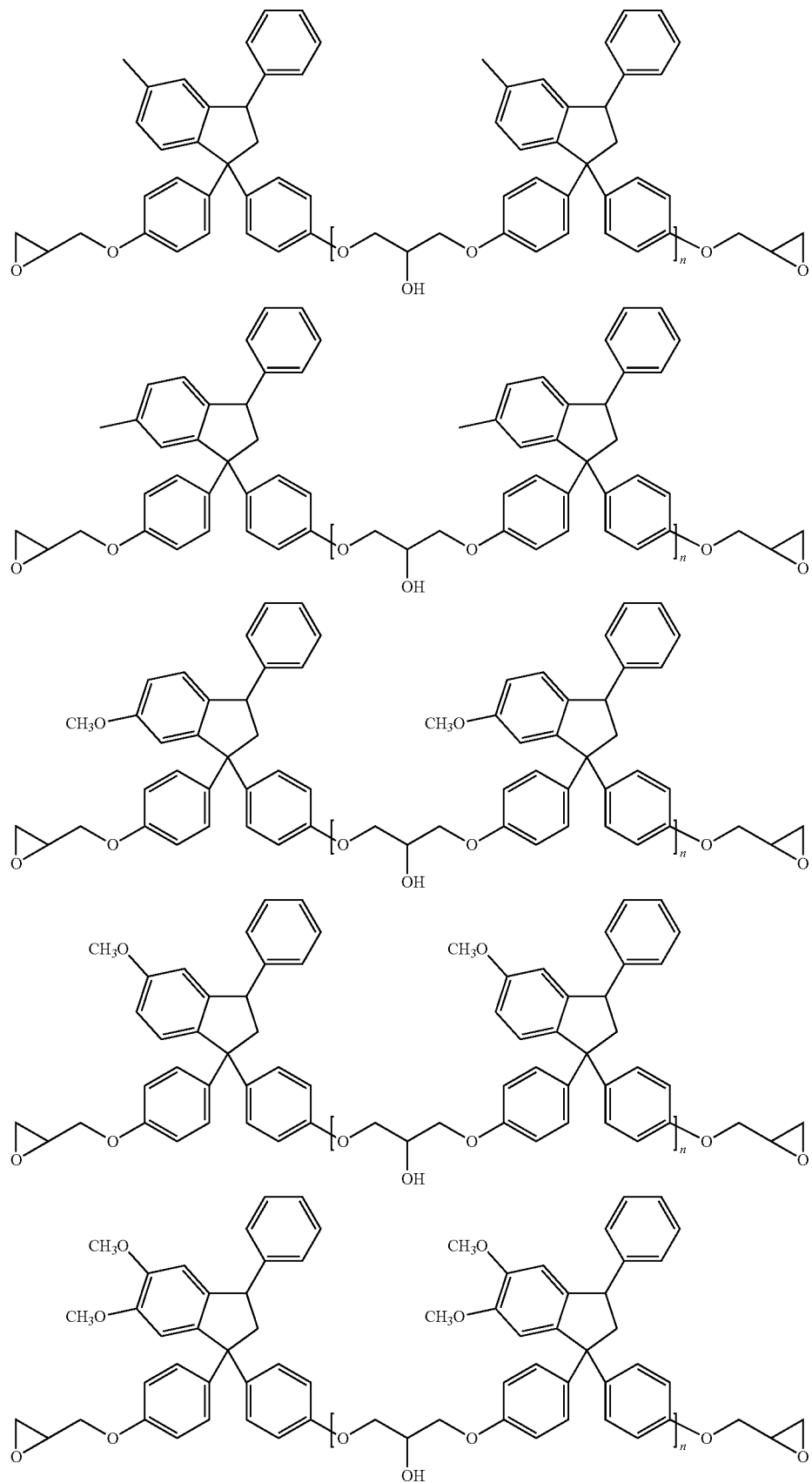

[Formula 5]
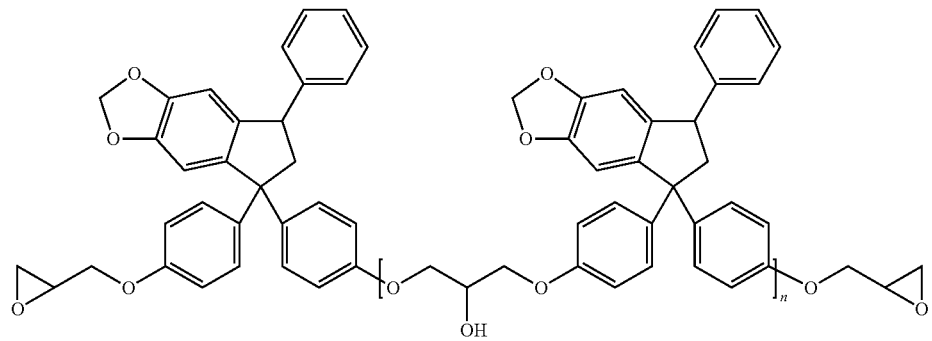
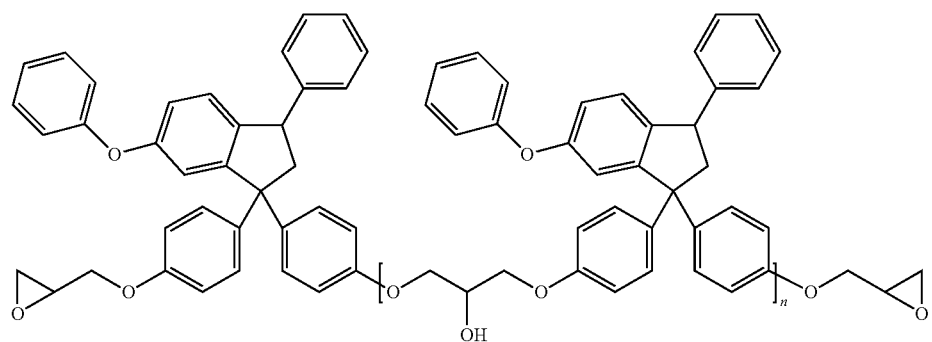
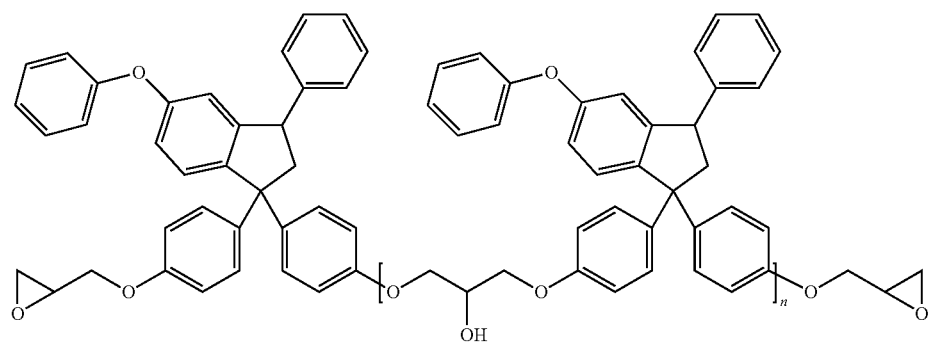
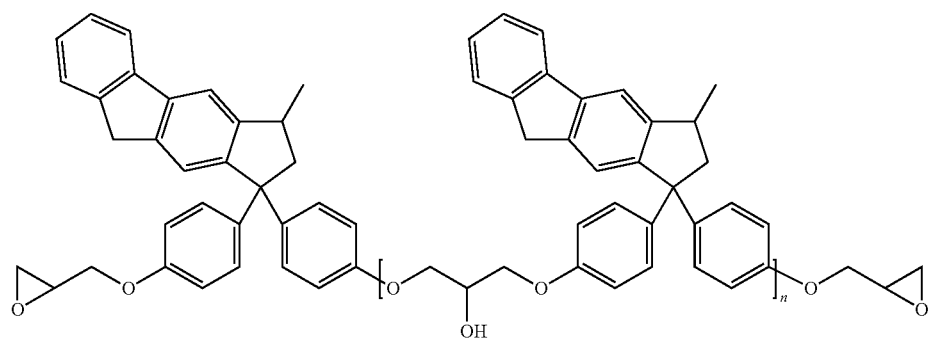

-continued
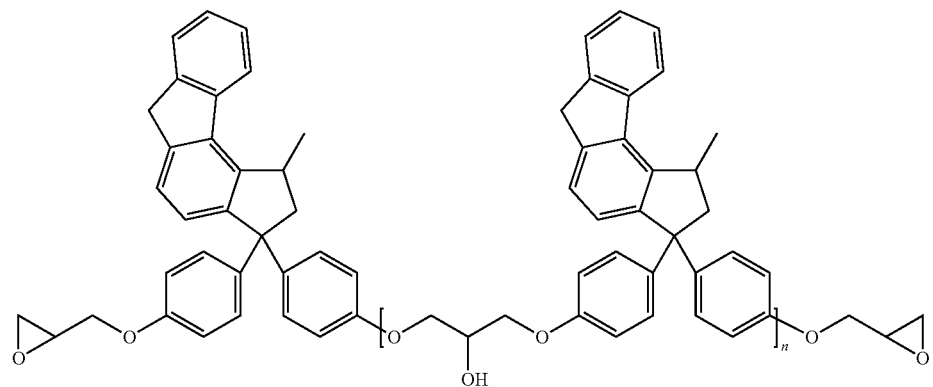
[Formula 6]
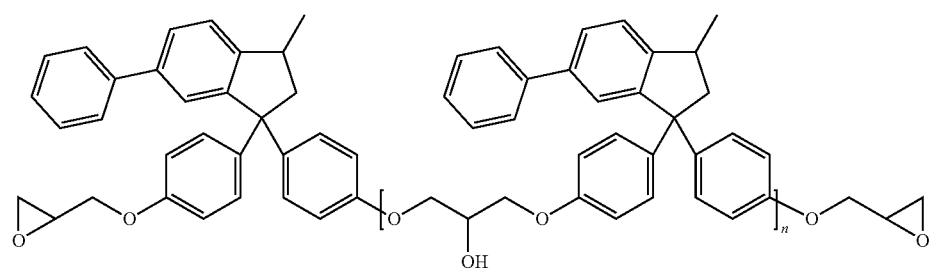
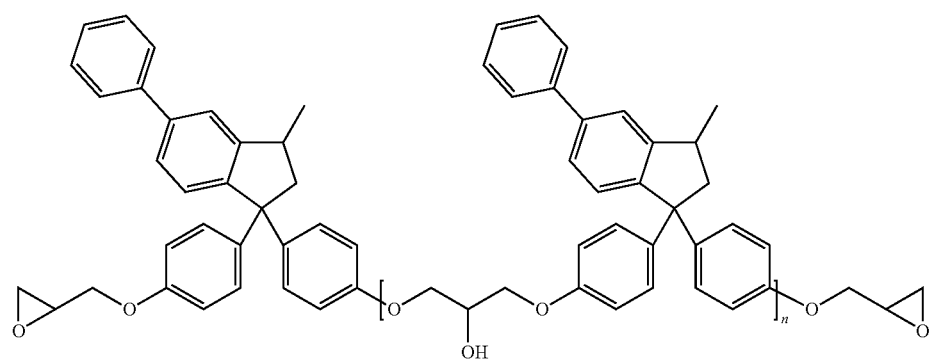
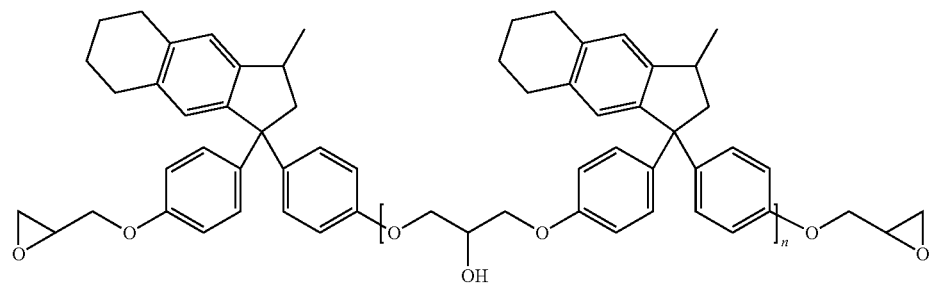
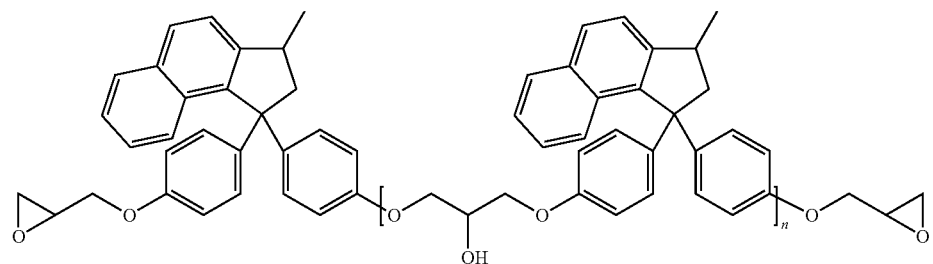

-continued
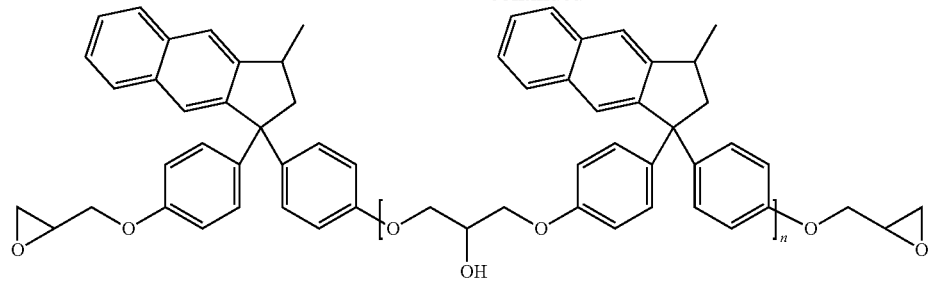
[Formula 7]
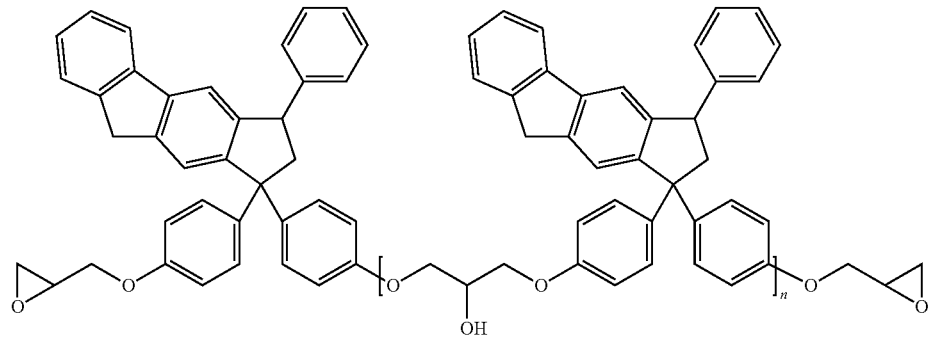
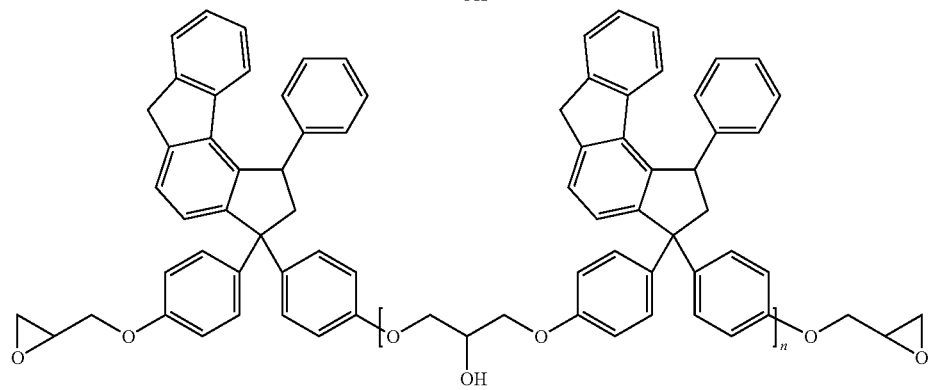
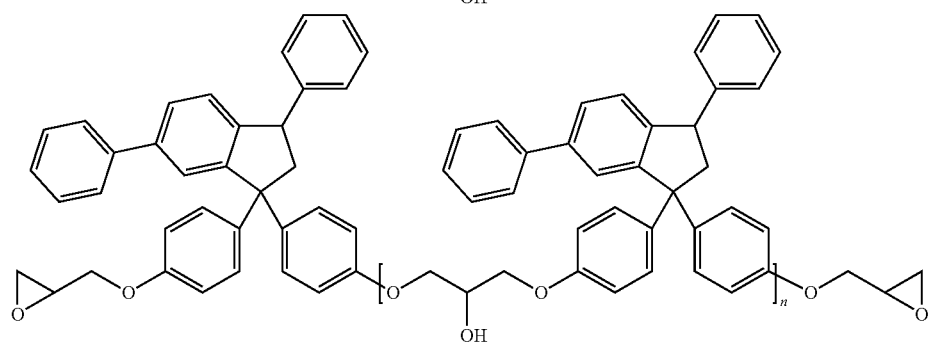
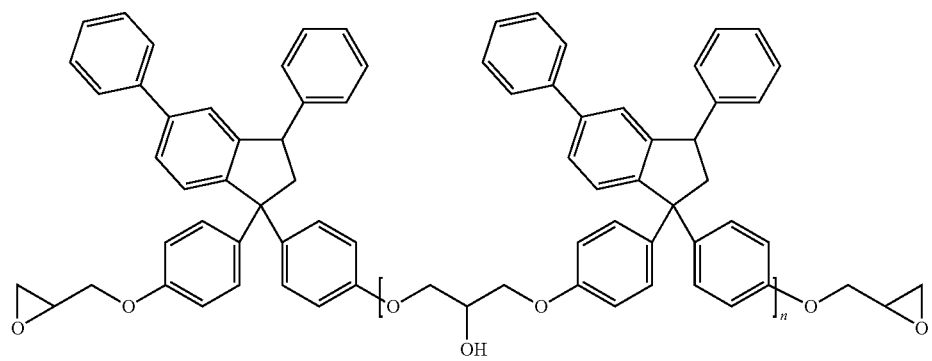

-continued
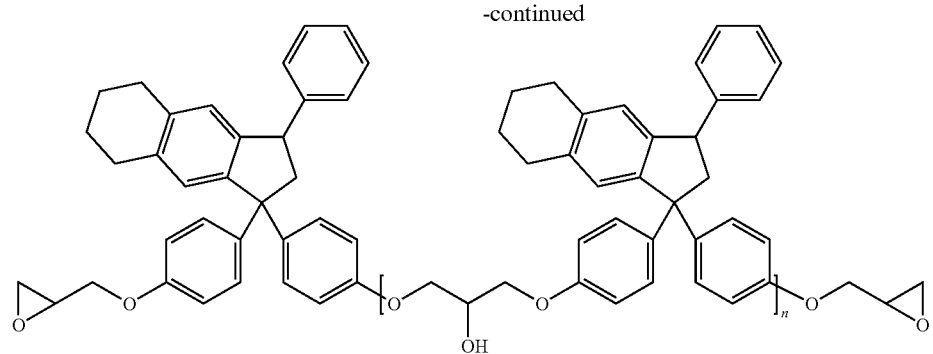
[Formula 8]
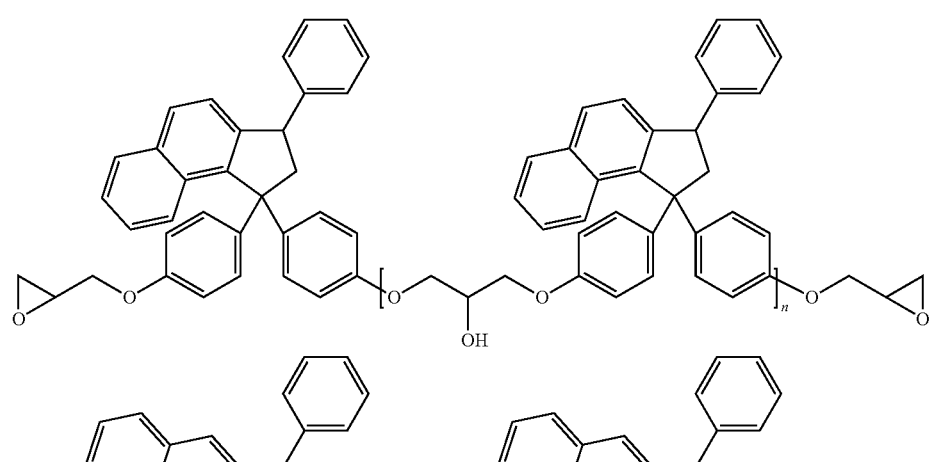
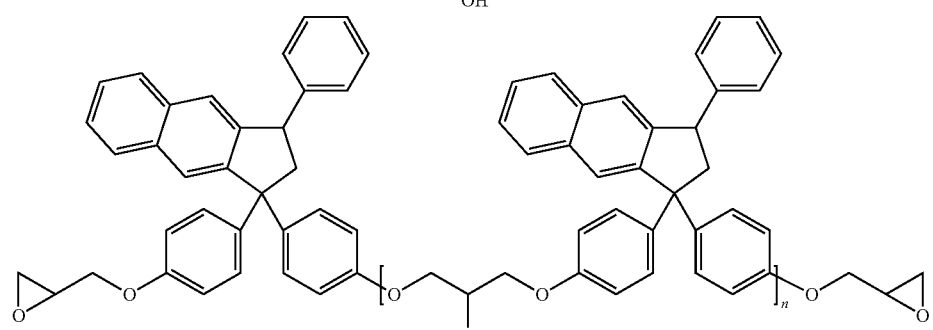
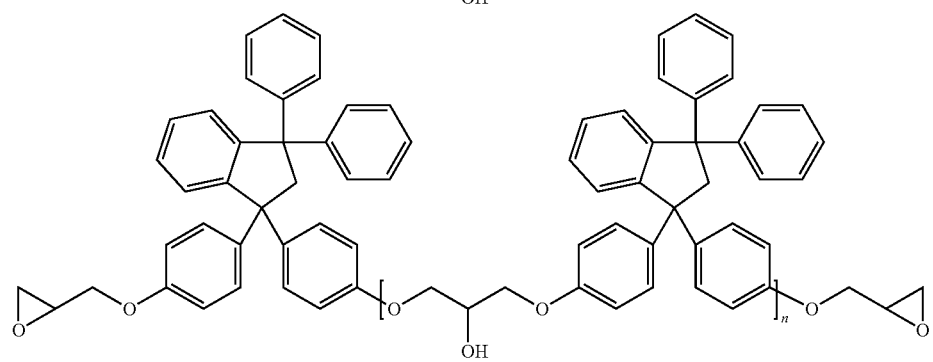
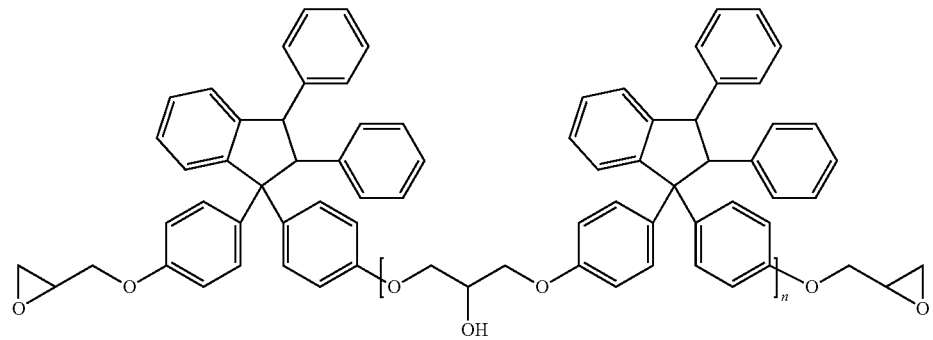

-continued
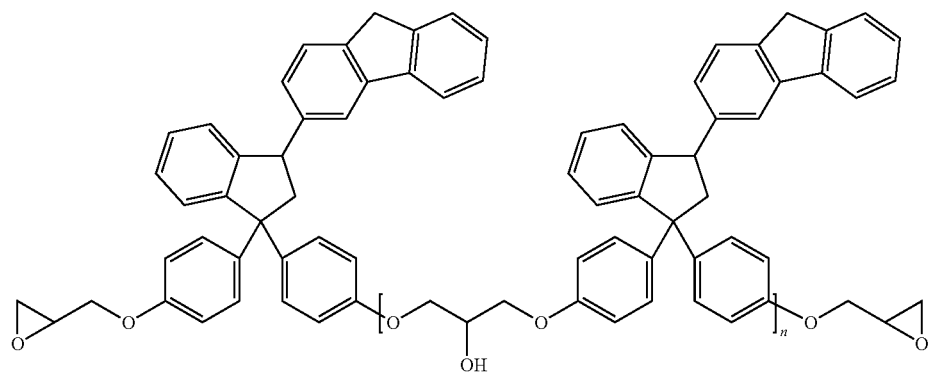
[Formula 9]
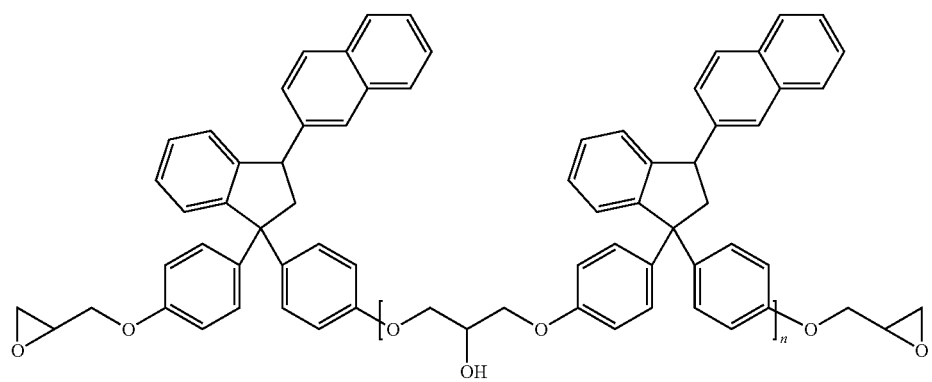
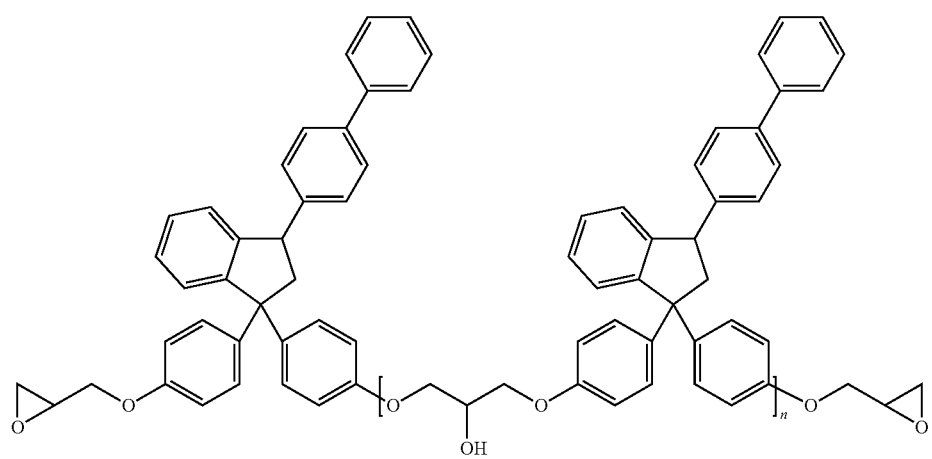
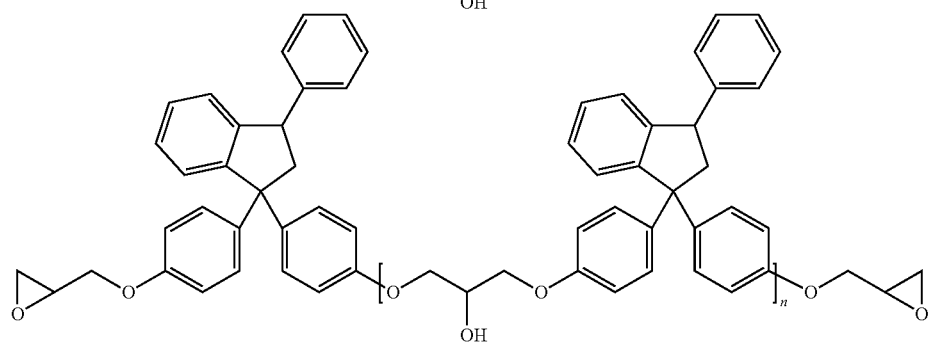
As regards the epoxy compound (A) of the present invention, preferred are those compounds in which x is 2 or 3; y is 0; X is an alkyl group having 1 to 10 carbon atoms, an aryl group having 2 to 20 carbon atoms, or a group that constitutes an aromatic ring when forming a ring with the other X; Y and Z are an alkyl group having 1 to 10 carbon atoms or an aryl group having 6 to 20 carbon atoms; and k, p, and r each independently represent 0 to 2. This is because materials therefor are easily available and such compounds have good productivity and hydrophobicity, thus having suitable characteristics for an epoxy resin.

There is no particular limitation to the method for producing the epoxy compound (A) of the present invention. For example, it is possible to easily produce the epoxy compound (A) of the present invention by first causing reaction between a benzo- or naphtho-cycloalkanone derivative (1) and a phenol derivative in the presence of an acidic catalyst to obtain a bisphenol compound (2) as an intermediate, and then causing reaction between this intermediate and epichlorohydrin in the presence of an alkali, a Lewis acid, or a phase-transfer catalyst. The production route is illustrated below. Note that X, Y, Z, k, p, r, x, y, and n in the following formula are as defined in the general formula (I).

[Formula 10]

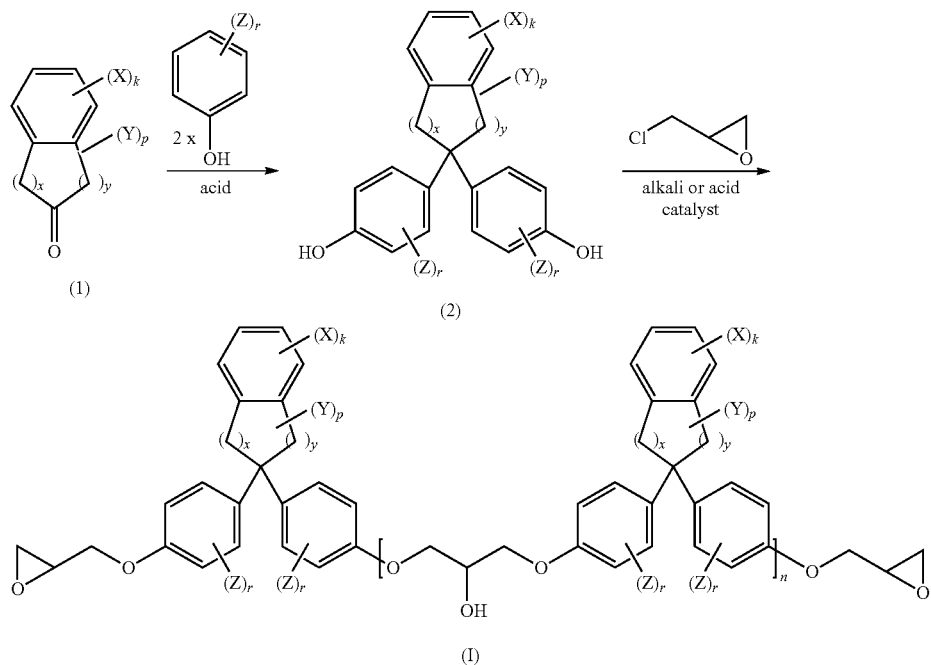

In producing the epoxy compound (A) of the present invention, a mixture including its optical isomers may be obtained; the mixture can be used, without any problems, within the scope of use of the present invention.

In the above production method, heretofore-known conditions may be adopted for producing the bisphenol compound (2) which is the intermediate. For example, the intermediate can be obtained by causing reaction for 1 to 40 hours at temperatures of 20 to 200° C. in the presence of an acidic catalyst.

Examples of the acidic catalyst include sulfonic acids, such as methane sulfonic acid, benzenesulfonic acid, m-xylene sulfonic acid, p-toluene sulfonic acid, hydroxymethyl sulfonic acid, 2-hydroxyethylsulfonic acid, hydroxypropyl sulfonic acid, trifluoromethane sulfonic acid, sulfosalicylic acid, and sulfophthalic acid; heteropoly acids, such as sulfuric acid, sulfuric anhydride, fuming sulfuric acid, chlorosulfuric acid, fluorosulfuric acid, hydrochloric acid, hydrogen chloride gas, oxalic acid, formic acid, phosphoric acid, trichloroacetic acid, trifluoroacetic acid, silicotungstic acid, and phosphotungstic acid; strongly acidic ion-exchange resins; activated clay; boron trifluoride; anhydrous aluminum chloride; and zinc chloride. Preferably 0.1 to 50 parts by mass, and more preferably 10 to 30 parts by mass, of the acidic catalyst is used with respect to 100 parts by mass of the benzocycloalkanone derivative (1).

A mercaptan catalyst may also be used to accelerate the reaction. Examples of the mercaptan catalyst include alkyl mercaptans, such as methyl mercaptan, ethyl mercaptan, propyl mercaptan, butyl mercaptan, octyl mercaptan, dodecyl mercaptan, and 1,6-hexanedithiol; aromatic mercaptans, such as thiophenol and thiocresol; mercapto organic acids, such as mercaptoacetic acid (thioglycolic acid), 3-mercaptopropionic acid, mercaptoundecanoic acid, and thiobenzoic acid; and heterocyclic mercaptans, such as 2-mercaptobenzothiazole.

Further, heretofore-known solvents may be used in the reaction. Examples of the solvents include aromatic hydrocarbon-based solvents, such as toluene, xylene, and cumene; terpene-based hydrocarbonic oils, such as turpentine, D-limonene, and pinene; paraffin-based solvents, such as mineral spirit, Swasol #310 (Cosmo Matsuyama Oil Co., Ltd.), and Solvesso #100 (Exxon Chemical Company); alcoholic solvents, such as methanol and ethanol; ester solvents, such as ethyl acetate; halogen-based solvents, such as dichloroethane, carbon tetrachloride, chloroform, trichloroethylene, methylene chloride, and chlorobenzene; cyclic ether-based solvents, such as tetrahydrofuran and dioxane; ethers; cellosolve-based solvents; ketone-based solvents; aniline; triethylamine; pyridine; dioxane; acetic acid; acetonitrile; and carbon disulfide.

Heretofore-known conditions may be adopted for producing the epoxy compound (A) of the present invention from the intermediate bisphenol compound (2) and epichlorohydrin. For example, it is preferable to carry out the reaction in temperatures of 20 to 100° C., and particularly 30 to 80° C., in the presence of an alkali, a Lewis acid, or a phase-transfer catalyst. Conditions below 20° C. result in slow reaction, requiring long time for the reaction. Conditions above 100° C. cause many side reactions, thus not being preferable.

Examples of alkalis used in the reaction include sodium hydroxide, potassium hydroxide, and calcium hydroxide. Examples of Lewis acids include the acidic catalysts illustrated above, and also tin tetrachloride, boron trifluoride, titanium tetrachloride, activated clay, aluminum chloride, magnesium chloride, potassium permanganate, and potassium chromate. Examples of phase-transfer catalysts include tetramethylammonium chloride, tetrabutylammonium bromide, methyltrioctylammonium chloride, methyltridecylammonium chloride, benzyltriethylammonium chloride, N,N-dimethylpyrrolidinium chloride, N-ethyl-N-methylpyrrolidinium iodide, N-butyl-N-methylpyrrolidinium bromide, N-benzyl-N-methylpyrrolidinium chloride, N-ethyl-N-methylpyrrolidinium bromide, N-butyl-N-methylmorpholinium bromide, N-butyl-N-methylmorpholinium iodide, N-allyl-N-methylmorpholinium bromide, N-methyl-N-benzylpiperidinium chloride, N-methyl-N-benzylpiperidinium bromide, N,N-dimethylpiperidinium iodide, N-methyl-N-ethylpiperidinium acetate, and N-methyl-N-ethylpiperidinium iodide.

In the present reaction, the amount of epichlorohydrin to be used is within the range of 1 mol or above, and particularly 2 to 10 mol, with respect to one hydroxyl group in the bisphenol compound (2). The amount of alkali to be used is within a range of 0.1 to 2.0 mol, and particularly 0.3 to 1.5 mol, with respect to one hydroxyl group in the bisphenol compound (2). The amount of Lewis acid or phase-transfer catalyst to be used is within a range of 0.01 to 10 mol %, and particularly 0.2 to 5 mol %, with respect to one hydroxyl group in the bisphenol compound (2).

Further, in the present reaction, it is possible to use such solvents as those given above in the section for producing the intermediate bisphenol compound (2). Further, an excessive amount of epichlorohydrin may be used as the solvent.

The epoxy compound (A) of the present invention can be made into an epoxy adduct (W) of the present invention by adding an unsaturated monobasic acid (B), to be used as a material for an alkali-developable resin composition and an alkali-developable photosensitive resin composition described further below, and can also be used as an epoxy resin composition of the present invention in combination with an epoxy-resin curing agent.

The epoxy resin composition of the present invention is a composition comprising the epoxy compound (A) of the present invention and a curing agent. Examples of the curing agent include polyalkyl polyamines, such as diethylenetriamine, triethylenetriamine, and tetraethylenepentamine; alicyclic polyamines, such as 1,2-diaminocyclohexane, 1,4-diamino-3,6-diethylcyclohexane, and isophorone diamine; and aromatic polyamines, such as m-xylylenediamine, diaminodiphenylmethane, and diaminodiphenylsulfone. Further examples include polyepoxy-addition-modified products produced by causing reaction, using ordinary methods, between the above polyamines and various epoxy resins, such as glycidyl ethers, e.g. phenylglycidyl ether, butylglycidyl ether, bisphenol A-diglycidyl ether, and bisphenol F-diglycidyl ether, or glycidyl esters thereof with carboxylic acids; amidation-modified products produced by causing reaction, using ordinary methods, between the above organic polyamines and carboxylic acids, such as phthalic acid, isophthalic acid, and dimer acid; and Mannich-modified products produced by causing reaction, using ordinary methods, among the above polyamine, an aldehyde such as formaldehyde, and a phenol that has on the nucleus at least one portion reactive to aldehydation, such as phenol, cresol, xylenol, t-butylphenol, and resorcin. Further, latent curing agents, such as dicyandiamide, acid anhydrides, and imidazoles such as 2-ethyl-4-methylimidazole, may be used.

In the epoxy resin composition of the present invention, the content of the curing agent is preferably 1 to 500 parts by mass, and more preferably 10 to 200 parts by mass, with respect to 100 parts by mass of the epoxy compound (A) of the present invention.

The epoxy resin composition of the present invention may further contain, as necessary, ordinarily-used additives, such as curing catalysts; reactive or non-reactive diluents (plasticizers), such as monoglycidyl ethers, dioctyl phthalate, dibutyl phthalate, benzyl alcohol, and coal tar; fillers or pigments, such as glass fiber, carbon fiber, cellulose, silica sand, cement, kaoline, clay, aluminum hydroxide, bentonite, talc, silica, powdered silica, titanium dioxide, carbon black, graphite, iron oxide, and bituminous substances; silane coupling agents, such as γ-aminopropyltriethoxy silane, N-β-(aminoethyl)-γ-aminopropyltriethoxy silane, N-β-(aminoethyl)-N'-β-(aminoethyl)-γ-aminopropyltriethoxy silane, γ-anilinopropyltriethoxy silane, γ-glycidoxypropyltriethoxy silane, β-(3,4-epoxycyclohexyl)ethyltriethoxy silane, vinyltriethoxy silane, N-β-(N-vinylbenzylaminoethyl)-γ-aminopropyltriethoxy silane, γ-methacryloxypropyltrimethoxy silane, γ-chloropropyltrimethoxy silane, and γ-mercaptopropyltrimethoxy silane; lubricants, such as candelilla wax, carnauba wax, Japan wax, Chinese wax, beeswax, lanolin, spermaceti wax, montan wax, petroleum wax, fatty acid wax, fatty acid ester, fatty acid ether, aromatic ester, and aromatic ether; thickening agents; thixotropic agents; antioxidants; light stabilizers; UV absorbers; fire retardants; antifoaming agents; rust preventives; colloidal silica, and colloidal alumina. Further, self-adhesive resins, such as xylene resin and petroleum resin, may be used with the above additives. In the epoxy resin composition of the present invention, the total amount of these optional additives is preferably equal to or below 100 parts by mass with respect to 100 parts by mass of the epoxy compound (A) of the present invention.

Further, the epoxy compound (A) of the present invention may be used as a material of various modified products, such as urethane modifications, silica modifications, phosphoric acid modifications, amine modifications, and (meth)acrylic acid modifications.

In addition to the above-described applications, the epoxy compound (A) of the present invention can find use in a wide variety of applications, such as coatings or adhesives for concrete, cement mortar, metals, leather, glass, rubber, plastics, wood, fabric, and paper; pressure-sensitive adhesives of packing adhesive tapes, self-adhesive labels, labels for frozen foods, removable labels, point-of-sale (POS) labels, self-adhesive wallpapers, and self-adhesive flooring materials; converted papers, such as art paper, lightweight coated paper, cast-coated paper, coated boards, carbonless copy paper, and impregnated paper; fiber treating agents, such as sizing agents, anti-fraying agents, and other processing agents for natural fibers, synthetic fibers, glass fiber, carbon fiber, and metal fibers; construction materials, such as sealing compounds, cement admixtures, and waterproofing compounds; and sealing materials for electronic and electric devices.

The epoxy adduct (W) of the present invention has a structure obtained by adding an unsaturated monobasic acid (B) to the epoxy compound (A) at such a ratio that the number of carboxyl groups in the unsaturated monobasic acid (B) is 0.1 to 1.0 with respect to one epoxy group in the epoxy compound (A). The epoxy adduct (W) is used as a material for the alkali-developable resin composition and the alkali-developable photosensitive resin composition of the present invention described further below, and is also useful as a material for photosensitive compositions for coatings.

It is preferable that the ratio of the carboxyl group in the unsaturated monobasic acid (B) is 0.3 to 1.0 with respect to one epoxy group in the epoxy compound (A).

The alkali-developable resin composition of the present invention contains one, or two or more, of the following: a photopolymerizable unsaturated compound (X) obtained by esterifying a polybasic acid anhydride (C) to the epoxy adduct (W) at such a ratio that the number of acid anhydride structures is 0.1 to 1.0 with respect to one hydroxyl group in the epoxy adduct (W); a photopolymerizable unsaturated compound (Y) obtained by further adding, as necessary, an epoxy compound (D) at such a ratio that the number of epoxy groups is 0.1 to 1.0 with respect to one hydroxyl group in the epoxy adduct (W); and a photopolymerizable unsaturated compound (Z) obtained by further esterifying, as necessary, a polybasic acid anhydride (E) at such a ratio that the number of acid anhydride structures is 0.1 to 1.0 with respect to one hydroxyl group in the epoxy adduct (W). Using different photopolymerizable unsaturated compounds (X), (Y), and (Z) for different situations facilitates adjustment of the acid value of the alkali-developable composition, and is thus useful in achieving a preferable development time.

It is preferable that, with respect to one hydroxyl group in the epoxy adduct (W), the ratio of the acid anhydride structure in the polybasic acid anhydride (C) is 0.3 to 0.95, the ratio of the epoxy group in the epoxy compound (D) is 0.3 to 0.9, and the ratio of the acid anhydride structure in the polybasic acid anhydride (E) is 0.3 to 0.7.

The unsaturated monobasic acid (B) used for preparing the alkali-developable resin composition of the present invention is used for improving the sensitivity of the alkali-developable resin composition, and examples thereof include acrylic acid, methacrylic acid, crotonic acid, cinnamic acid, sorbic acid, hydroxyethyl methacrylate malate, hydroxyethyl acrylate malate, hydroxypropyl methacrylate malate, hydroxypropyl acrylate malate, dicyclopentadiene malate, or multi-functional (meth)acrylates having one carboxyl group and two or more (meth)acryloyl groups.

The multi-functional (meth)acrylate having one carboxyl group and two or more (meth)acryloyl groups can be obtained, for example, by causing reaction between a multi-functional (meth)acrylate having one hydroxyl group and two or more (meth)acryloyl groups in one molecule, and a dibasic acid anhydride or a carboxylic acid.

Examples of multi-functional (meth)acrylates having one carboxyl group and two or more (meth)acryloyl groups may include compounds shown in [Formula 11] to [Formula 13] below.

[Formula 11]

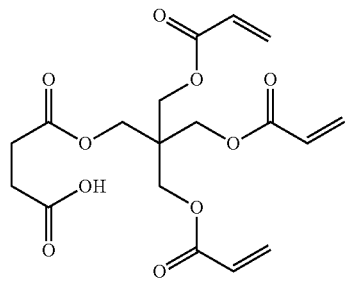

[Formula 12]

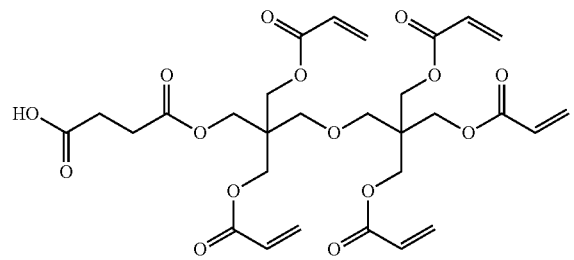

[Formula 13]

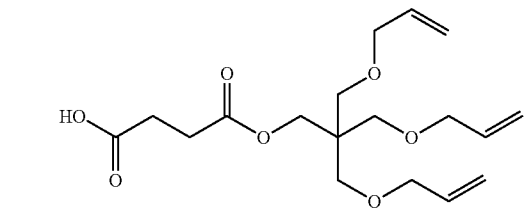

Examples of the polybasic acid anhydride (C) used for obtaining the alkali-developable resin composition of the present invention include monoanhydrides, such as succinic anhydride, maleic anhydride, trimellitic anhydride, phthalic anhydride, methyltetrahydrophthalic anhydride, tetrahydrophthalic anhydride, nadic anhydride, methylnadic anhydride, a trialkyltetrahydrophthalic anhydride, hexahydrophthalic anhydride, a trialkyltetrahydrophthalic anhydride-maleic anhydride adduct, dodecenylsuccinic anhydride, methylhymic anhydride, and methylhexahydrophthalic anhydride; dianhydrides, such as 3,3',4,4'-biphenyltetracarboxylic dianhydride, 3,3',4,4'-diphenyltetrasulfonic dianhydride, 4,4'-oxydiphthalic dianhydride, 2,3,5-tricarboxycyclopentylacetic dianhydride, 1,2,3,4-cyclopentanetetracarboxylic dianhydride, pyromellitic anhydride, 2,2',3,3'-benzophenonetetracarboxylic anhydride, 5-(2,5-dioxotetrahydrofuryl)-3-methyl-3-cyclohexene-1,2-dicarboxylic anhydride, 3,3',4,4'-benzophenonetetracarboxylic anhydride, ethylene glycol bisanhydrotrimellitate, and meso-butane-1,2,3,4-tetracarboxylic anhydride; and trianhydrides, such as glycerol trisanhydrotrimellitate. Inter alia, a dianhydride or a combination of a dianhydride and a monoanhydride is preferred.

Examples of the epoxy compound (D) used for preparing the alkali-developable resin composition of the invention include monofunctional epoxy compounds, multi-functional epoxy compounds, or the epoxy compound (A) of the present invention. The monofunctional epoxy compound is used for adjusting the acid value of the alkali-developable resin composition, and examples thereof include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxy glycidyl ether, p-butylphenol glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexane monoxide, 1,2-epoxy-4-vinylcyclohexane, styrene oxide, pinene oxide, methylstyrene oxide, cyclohexene oxide, propylene oxide, and compounds shown in [Formula 14] to [Formula 17] below.

[Formula 14]

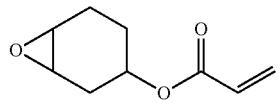

[Formula 15]

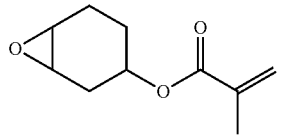

[Formula 16]

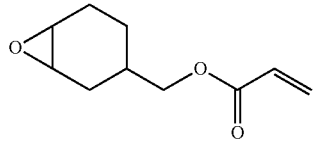

[Formula 17]

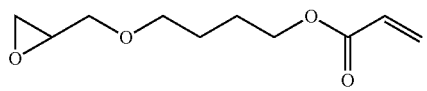

The multi-functional epoxy compound is used to increase the molecular weight of the photopolymerizable unsaturated compound and thereby adjust the development speed, and examples that can be used include bisphenol type epoxy compounds and glycidyl ethers.

It is possible to use, as the bisphenol type epoxy compound, an alkylidene bisphenol polyglycidyl ether type epoxy resin as well as a bisphenol type epoxy compound such as a hydrogenated bisphenol type epoxy compound.

Examples of the glycidyl ethers include ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane, 1,1,1-tri(glycidyloxymethyl)methane, and 1,1,1,1-tetra(glycidyloxymethyl)methane.

It is also possible to use, as the multi-functional epoxy compound, novolac type epoxy compounds, such as a phenol novolac type epoxy compound, a biphenyl novolac type epoxy compound, a cresol novolac type epoxy compound, a bisphenol A novolac type epoxy compound, and a dicyclopentadiene novolac type epoxy compound; alicyclic epoxy compounds, such as 3,4-epoxy-6-methylcyclohexylmethyl-3',4'-epoxy-6'-methylcyclohexane carboxylate, 3,4-epoxycyclohexylmethyl-3',4'-epoxycyclohexane carboxylate, and 1-epoxyethyl-3,4-epoxycyclohexane; glycidyl esters, such as phthalic acid diglycidyl ester, tetrahydrophthalic acid diglycidyl ester, and dimer acid glycidyl ester; glycidyl amines, such as tetraglycidyl diaminodiphenylmethane, triglycidyl-p-aminophenol, and N,N-diglycidyl aniline; heterocyclic epoxy compounds, such as 1,3-diglycidyl-5,5-dimethylhydantoin and triglycidyl isocyanurate; dioxide compounds, such as dicyclopentadiene dioxide; naphthalene type epoxy compounds, triphenylmethane type epoxy compounds, and dicyclopentadiene type epoxy compounds.

The examples given above for the polybasic acid anhydride (C) may be used as the polybasic acid anhydride (E) used as necessary for obtaining the alkali-developable resin composition of the present invention.

It is possible to repeat the reaction of adding the epoxy compound (D) and then esterifying the polybasic acid anhydride (E) to the photopolymerizable unsaturated compound having a structure obtained by causing reaction among the components (A) to (E). Also, it is possible to add the epoxy compound (D) and then esterify a lactone compound, instead of the polybasic acid anhydride (E), to the photopolymerizable unsaturated compound having a structure obtained by causing reaction among the components (A) to (E).

The content of the photopolymerizable unsaturated compound (X), (Y), or (Z) having a structure obtained by causing reaction among the components (A) to (E) is preferably 1 to 70% by mass, and more preferably 3 to 30% by mass, in the alkali-developable resin composition of the present invention, and the acid value of the solids content ranges preferably from 20 to 100 mgKOH/g, and more preferably from 50 to 100 mgKOH/g.

The alkali-developable resin composition of the present invention may contain solvents in addition to the photopolymerizable unsaturated compound(s). For example, in order to bring the content of the photopolymerizable unsaturated compound within the above-described preferable range, a solvent may be used for the remainder other than the photopolymerizable unsaturated compound. Specific examples of such solvents include the examples given as the solvent used in the later-described alkali-developable photosensitive resin composition. The solvent used in synthesizing the photopolymerizable unsaturated compound from the components (A) to (E) may be kept as-is in the alkali-developable resin composition of the present invention, without removal. Further, one type of compound may be used singly for each component (A) to (E), or two or more types may be used mixed together.

The alkali-developable resin composition of the present invention is used for an alkali-developable photosensitive resin composition, primarily by being mixed with a photopolymerization initiator (F) and a solvent.

The following describes this alkali-developable photosensitive resin composition (also referred to hereinafter as "alkali-developable photosensitive resin composition of the present invention") according to preferred embodiments thereof.

The alkali-developable photosensitive resin composition of the present invention at least contains a photopolymerization initiator (F) in addition to the alkali-developable resin composition of the present invention which contains the photopolymerizable unsaturated compound.

In the alkali-developable photosensitive resin composition of the present invention, the content of the photopolymerizable unsaturated compound is preferably 50 to 90% by mass, and more preferably 60 to 80% by mass, in terms of its rate with respect to the total mass of the total solids content, which remains after removing the solvent from the alkali-developable photosensitive resin composition.

Heretofore-known compounds may be used as the photopolymerization initiator (F), and examples include benzoyl peroxide, 2,2'-azobisisobutyronitrile, benzophenone, phenyl biphenyl ketone, 1-hydroxy-1-benzoylcyclohexane, benzil, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1,7-bis(9'-acridinyl)heptane, 9-n-butyl-3,6-bis(2'-morpholinoisobutyroyl)carbazole, 2-methyl-1-[4-(methylthio)phenyl]-2-morpholinopropan-1-one, p-methoxyphenyl-2,4-bis(trichloromethyl)-s-triazine, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2-(p-butoxystyryl)-s-triazine, 2-(p-butoxystyryl)-5-trichloromethyl-1,3,4-oxadiazole, 9-phenylacridine, 9,10-dimethylbenzphenazine, benzophenone/Michler's ketone, hexaarylbiimidazole/mercaptobenzimidazole, thioxanthone/amine, and bis(2,4,6-trimethylbenzoyl)-phenylphosphine oxide, as well as compounds disclosed in JP-A-2000-80068, JP-A-2001-233842, JP-A-2005-97141, JP-T-2006-516246, Japanese Patent No. 3860170, Japanese Patent No. 3798008, and WO2006/018973. Inter alia, compounds represented by the following general formula (a) or (c) are preferred.

[Formula 18]

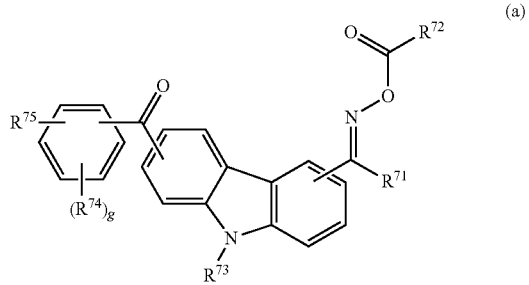

wherein, $R^{71}$, $R^{72}$, and $R^{73}$ each independently represent R, OR, COR, SR, CONRR', or CN; R and R' each independently represent an alkyl group, an aryl group, an arylalkyl group, or a heterocyclic group; the above may be substituted with a halogen atom and/or a heterocyclic group; among the above, an alkylene portion of the alkyl group and the arylalkyl group may be interrupted by an unsaturated bond, an ether bond, a thioether bond, or an ester bond; R and R' may be taken together to form a ring; $R^{74}$ represents a halogen atom or an alkyl group; $R^{75}$ represents a hydrogen atom, a halogen atom, an alkyl group, or a substituent represented by the following general formula (b); g is an integer of 0 to 4; and in case g is equal to or above 2, the plurality of $R^{74}$ may represent different groups.

[Formula 19]

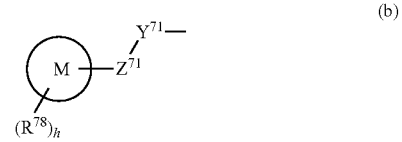

wherein, ring M represents a cycloalkane ring, an aromatic ring, or a heterocycle; $R^{76}$ represents a halogen atom or an alkyl group; $Y^{71}$ represents an oxygen atom, a sulfur atom, or a selenium atom; $Z^{71}$ represents an alkylene group having 1 to 5 carbon atoms; h is an integer of 0 to 4; and in case h is equal to or above 2, the plurality of $R^{76}$ may represent different groups.

[Formula 20]

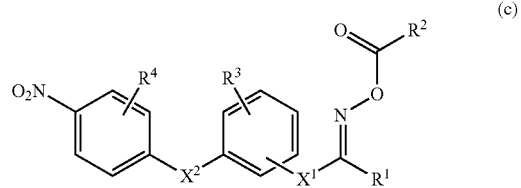

wherein, $R^1$ and $R^2$ each independently represent $R^{11}$, $OR^{11}$, $COR^{11}$, $SR^{11}$, $CONR^{12}R^{13}$, or CN; $R^{11}$, $R^{12}$, and $R^{13}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms; a hydrogen atom of the alkyl group, the aryl group, the arylalkyl group, and the heterocyclic group may further be substituted with $OR^{21}$, $COR^{21}$, $SR^{21}$, $NR^{22}R^{23}$, $CONR^{22}R^{23}$, $-NR^{22}-OR^{23}-NCOR^{22}-OCOR^{23}$, $-C(=N-OR^{21})-R^{22}$, $-C(=N-OCOR^{21})-R^{22}$, CN, a halogen atom, $-CR^{21}=CR^{22}R^{23}$, $-CO-CR^{21}=CR^{22}R^{23}$ a carboxyl group, or an epoxy group; $R^{21}$, $R^{22}$, and $R^{23}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms; a methylene group of an alkylene portion of substituents represented by the above $R^{11}$, $R^{12}$, $R^{13}$, $R^{21}$, $R^{22}$, and $R^{23}$ may be interrupted 1 to 5 times by an unsaturated bond, an ether bond, a thioether bond, an ester bond, a thioester bond, an amide bond, or an urethane bond; an alkyl portion of the above substituents may have a branched side chain or may be a cyclic alkyl; an alkyl end of the above substituents may be an unsaturated bond; and $R^{12}$ and $R^{13}$, as well as $R^{22}$ and $R^{23}$, may respectively be taken together to form a ring. $R^3$ and $R^4$ each independently represent $R^{11}$, $OR^{11}$, $SR^{11}$, $COR^{11}$, $CONR^{12}R^{13}$, $NR^{12}COR^{11}$, $OCOR^{11}$, $COOR^{11}$, $SCOR^{11}$, $OCSR^{11}$, $COSR^{11}$, $CSOR^{11}$, CN, a halogen atom, or a hydroxyl group; and a and b each independently represent 0 to 4. $X^1$ represents a direct bond or CO; $X^2$ represents an oxygen atom, a sulfur atom, a selenium atom, $CR^{31}R^{32}$, CO, $NR^{33}$ or $PR^{34}$; $R^{31}$, $R^{32}$, $R^{33}$, and $R^{34}$ each independently represent $R^{11}$, $OR^{11}$, $COR^{11}$, $SR^{11}$, $CONR^{12}R^{13}$, or CN; $R^3$ may bond with one of the carbon atoms of the adjacent benzene ring across-$X^2$- to form a ring structure, or $R^3$ and $R^4$ may be taken together to form a ring; and $R^{31}$, $R^{33}$, and $R^{34}$ each independently may be taken together with either one of the adjacent benzene rings to form a ring.

In the alkali-developable photosensitive resin composition of the present invention, the content of the photopolymerization initiator (F) is preferably 0.1 to 40% by mass, and more preferably 1.0 to 10% by mass, in terms of its rate with respect to the total mass of the total solids content, which remains after removing the solvent from the alkali-developable photosensitive resin composition. One type of photopolymerization initiator (F) may be used, or two or more types may be used mixed together.

There is no particular limitation to the solvent to be contained in the alkali-developable photosensitive resin composition of the present invention as long as the solvent is generally capable of dissolving or dispersing the above components, and examples thereof include ketones, such as methylethyl ketone, methylamyl ketone, diethyl ketone, acetone, methylisopropyl ketone, methylisobutyl ketone, and cyclohexanone; ether-based solvents, such as ethyl ether, dioxane, tetrahydrofuran, 1,2-dimethoxyethane, 1,2-diethoxyethane, and dipropylene glycol dimethyl ether; ester-based solvents, such as methyl acetate, ethyl acetate, n-propyl acetate, isopropyl acetate, and n-butyl acetate; cellosolve-based solvents, such as ethylene glycol monomethyl ether, ethylene glycol monoethyl ether, and propylene glycol monomethyl ether acetate; alcohol-based solvents, such as methanol, ethanol, iso- or n-propanol, iso- or n-butanol, and amyl alcohol; BTX-based solvents, such as benzene, toluene, and xylene; aliphatic hydrocarbon-based solvents, such as hexane, heptane, octane, and cyclohexane; terpene-based hydrocarbonic oils, such as turpentine, D-limonene, and pinene; paraffin-based solvents, such as mineral spirit, Swasol #310 (Cosmo Matsuyama Oil Co., Ltd.), and Solvesso #100 (Exxon Chemical Company); halogenated aliphatic hydrocarbon-based solvents, such as carbon tetrachloride, chloroform, trichloroethylene, and methylene chloride; halogenated aromatic hydrocarbon-based solvents, such as chlorobenzene; as well as Carbitol-based solvents, aniline, triethylamine, pyridine, acetic acid, acetonitrile, carbon disulfide, N,N-dimethylformamide, and N-methyl pyrrolidone. Inter alia, ketones or cellosolve-based solvents are preferred. One type of these solvents may be used, or two or more types may be used mixed together.

In the alkali-developable photosensitive resin composition of the present invention, the content of the solvent may be adjusted so that the concentration of the total solids content with respect to the alkali-developable photosensitive resin composition is preferably 5 to 40% by mass, and more preferably 15 to 30% by mass.

An alkali-developable, colored photosensitive resin composition of the present invention contains a colorant (G) in addition to the alkali-developable photosensitive resin composition.

Any known pigment used for manufacturing heretofore color filters may be employed as the pigment used as the colorant (G) in the alkali-developable, colored photosensitive resin composition of the present invention. Specific examples of organic pigments are shown below by their color index (C.I.) numbers. Note that in the list below, "x" represents an integer that can be freely selected from the C.I. number.

Pigment Blue:
C.I.: 1, 1:2, 1:x, 9:x, 15, 15:1, 15:2, 15:3, 15:4, 15:5, 15:6, 16, 24, 24:x, 56, 60, 61, and 62

Pigment Green:
C.I.: 1, 1:x, 2, 2:x, 4, 7, 10, and 36

Pigment Orange:
C.I.: 2, 5, 13, 16, 17:1, 31, 34, 36, 38, 43, 46, 48, 49, 51, 52, 59, 60, 61, 62, and 64

Pigment Red:
C.I.: 1, 2, 3, 4, 5, 6, 7, 9, 10, 14, 17, 22, 23, 31, 38, 41, 48:1, 48:2, 48:3, 48:4, 49, 49:1, 49:2, 52:1, 52:2, 53:1, 57:1, 60:1, 63:1, 66, 67, 81:1, 81:3, 81:x, 83, 88, 90, 112, 119, 122, 123, 144, 146, 149, 166, 168, 169, 170, 171, 172, 175, 176, 177, 178, 179, 184, 185, 187, 188, 190, 200, 202, 206, 207, 208, 209, 210, 216, 224, and 226

Pigment Violet:
C.I.: 1, 1:x, 3, 3:3, 3:x, 5:1, 19, 23, 27, 32, and 42

Pigment Yellow:
C.I.: 1, 3, 12, 13, 14, 16, 17, 24, 55, 60, 65, 73, 74, 81, 83, 93, 95, 97, 98, 100, 101, 104, 106, 108, 109, 110, 113, 114, 116, 117, 119, 120, 126, 127, 128, 129, 138, 139, 150, 151, 152, 153, 154, 156, and 175

Further, examples of black pigments include carbon blacks #2400, #2350, #2300, #2200, #1000, #980, #970, #960, #950, #900, #850, MCF88, #650, MA600, MA7, MA8, MA11, MA100, MA220, IL30B, IL31B, IL7B, IL11B, IL52B, #4000, #4010, #55, #52, #50, #47, #45, #44, #40, #33, #32, #30, #20, #10, #5, CF9, #3050, #3150, #3250, #3750, and #3950, Dia Black A, Dia Black N220M, Dia Black N234, Dia Black I, Dia Black LI, Dia Black LH, Dia Black N339, Dia Black SH, Dia Black SHA, Dia Black LH, Dia Black H, Dia Black HA, Dia Black SF, Dia Black N550M, Dia Black E, Dia Black G, Dia Black R, Dia Black N760M, and Dia Black LR, which are all manufactured by Mitsubishi Chemical Corp.; Thermax series N990, N991, N907, N908, N990, N991, and N908, which are carbon blacks manufactured by Cancarb Ltd.; ASAHI #80, ASAHI #70, ASAHI #70L, ASAHI F-200, ASAHI #66, ASAHI #66U, ASAHI #50, ASAHI #35, ASAHI #15, and ASAHI Thermal, which are carbon blacks manufactured by Asahi Carbon Co., Ltd.; and Color Black Fw200, Color Black Fw2, Color Black Fw2V, Color Black Fw1, Color Black Fw18, Color Black S170, Color Black S160, Special Black 6, Special Black 5, Special Black 4, Special Black 4A, Special Black 250, Special Black 350, Printex U, Printex V, Printex 140U, and Printex 140V, which are carbon blacks manufactured by Degussa (all trade names).

Other pigments that can be used include inorganic pigments, such as Milori blue, iron oxide, titanium oxide, calcium carbonate, magnesium carbonate, silica, alumina, cobalt-based pigments, manganese-based pigments, talc, chromates, ferrocyanides, sulfates of various metals, sulfides, selenides, phosphates, ultramarine blue, iron blue, cobalt blue, cerulean blue, viridian, emerald green, and cobalt green. One type of these pigments may be used, or two or more types may be used mixed together.

Examples of dyes that can be used as the colorant (G) include azo dyes, anthraquinone dyes, indigoid dyes, triarylmethane dyes, xanthene dyes, alizarine dyes, acridine dyes, stilbene dyes, thiazole dyes, naphthol dyes, quinoline dyes, nitro dyes, indamine dyes, oxazine dyes, phthalocyanine dyes, and cyanine dyes. One type of these dyes may be used, or two or more types may be used mixed together.

In the alkali-developable, colored photosensitive resin composition of the present invention, the content of the colorant (G) is preferably 0.5 to 70% by mass, and more preferably 5 to 60% by mass, in terms of its rate with respect to the total mass of the total solids content, which remains after removing the solvent from the alkali-developable, colored photosensitive resin composition.

It is also possible to use, for example, a monomer having an unsaturated bond, a chain transfer agent, and/or a surfactant in the alkali-developable resin composition, the alkali-developable photosensitive resin composition, and the alkali-developable, colored photosensitive resin composition of the present invention.

Examples of the monomer having an unsaturated bond include 2-hydroxyethyl acrylate, 2-hydroxypropyl acrylate, isobutyl acrylate, n-octyl acrylate, isooctyl acrylate, isononyl acrylate, stearyl acrylate, methoxyethyl acrylate, dimethylaminoethyl acrylate, zinc acrylate, 1,6-hexanediol diacrylate, trimethylolpropane triacrylate, 2-hydroxyethyl methacrylate, 2-hydroxypropyl methacrylate, butyl methacrylate, t-butyl methacrylate, cyclohexyl methacrylate, trimethylolpropane trimethacrylate, dipentaerythritol pentaacrylate, dipentaerythritol hexaacrylate, pentaerythritol tetraacrylate, pentaerythritol triacrylate, and tricyclodecane dimethylol diacrylate.

In the alkali-developable photosensitive resin composition of the present invention, the content of the monomer having an unsaturated bond is preferably 0.01 to 20% by mass, and more preferably 0.1 to 10% by mass, in terms of its rate with respect to the total mass of the total solids content, which remains after removing the solvent from the alkali-developable photosensitive resin composition. One type of the above compounds may be used, or two or more types may be used mixed together.

The chain transfer agent includes mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the above mercapto compounds; and iodized alkyl compounds, such as iodoacetic acid, iodopropionic acid, 2-iodoethanol, 2-iodoethanesulfonic acid, and 3-iodopropanesulfonic acid. One type of the above compounds may be used, or two or more types may be used mixed together.

The surfactant that can be used includes fluorine-containing surfactants, such as perfluoroalkylphosphoric esters and perfluoroalkylcarboxylic acid salts; anionic surfactants, such as higher fatty acid alkali salts, alkylsulfonates, and alkylsulfates; cationic surfactants, such as higher amine halogenic acid salts and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants, and silicone-based surfactants. One type of the above compounds may be used, or two or more types may be used mixed together.

The alkali-developable resin composition, the alkali-developable photosensitive resin composition, and the alkali-developable, colored photosensitive resin composition of the invention can further contain a thermoplastic organic polymer to improve the characteristics of its cured product. Examples of the thermoplastic organic polymer include polystyrene, polymethyl methacrylate, a methyl methacrylate-ethyl acrylate copolymer, poly(meth)acrylic acid, a styrene-(meth)acrylic acid copolymer, a (meth)acrylic acid-methyl methacrylate copolymer, polyvinyl butyral, cellulose esters, polyacrylamide, and saturated polyesters. One type of the above compounds may be used, or two or more types may be used mixed together.

The alkali-developable resin composition, the alkali-developable photosensitive resin composition, and the alkali-developable, colored photosensitive resin composition of the invention may further contain, as necessary, commonly employed additives, such as a thermal polymerization suppressor, e.g. anisole, hydroquinone, pyrocatechol, t-butyl catechol, and phenothiazine; a plasticizer; an adhesion accelerator; a filler; an antifoaming agent; a dispersing agent; a leveling agent; a silane coupling agent; and a fire retardant. One type of the above compounds may be used, or two or more types may be used mixed together.

The alkali-developable photosensitive resin composition and the alkali-developable, colored photosensitive resin composition of the present invention are applicable onto a substrate, such as metal, paper, and plastic, using known means, such as a spin coater, a bar coater, a roll coater, a curtain coater, various screen printing techniques, inkjet printing, or immersion. Also, after once being applied onto a substrate such as a film, the composition may be transferred onto another substrate, the application method therefor not being particularly limited.

The alkali-developable, (colored) photosensitive resin composition of the present invention is used for an alkali-developable, (colored) photosensitive resin composition, primarily by being mixed with the above-described solvent, the above-described photopolymerization initiator, and the colorant. The alkali-developable, (colored) photosensitive resin composition is not particularly limited in terms of its application, and can find use in a variety of applications, such as photo-curing coatings, photo-curing adhesives, printing plates, and photoresists for printed wiring boards, as well as for forming projections for liquid-crystal multi-domain alignment control or pixels in color filters, which are used in liquid-crystal displays, plasma displays, electroluminescent panels, video cameras, and so forth.

Usable light sources that emit active light for curing the alkali-developable photosensitive resin composition and the alkali-developable, colored photosensitive resin composition of the present invention may include those emitting light having wavelengths between 300 and 450 nm, and examples that can be used include an ultrahigh pressure mercury lamp, a mercury vapor arc lamp, a carbon arc lamp, and a xenon arc lamp.

EXAMPLES

The present invention is described in further detail below with reference to Examples and Comparative Examples, but the invention is not to be limited thereto.

Note that Examples 1-1 to 1-3 illustrate examples of producing an epoxy compound (A) and an epoxy adduct (W) of the present invention, Usage Example 1 illustrates an example of an epoxy resin composition using an epoxy compound (A) of the present invention, Examples 2-1 to 2-7 illustrate examples of producing alkali-developable resin compositions of the present invention, Examples 3-1 to 3-7 illustrate examples of alkali-developable photosensitive resin compositions of the present invention, and Examples 4-1 to 4-7 illustrate examples of alkali-developable, colored photosensitive resin compositions of the present invention.

Example 1-1

Step 1

Producing 1,1-bis(4-hydroxyphenyl)indan (Bisphenol Compound (2); Also Referred to Hereinafter as Compound P-1)

[Formula 21]

Compound P-1

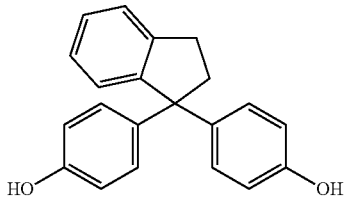

To a 2 L four-neck flask equipped with a stirrer, a nitrogen inlet, a reflux condenser, and a thermometer were put, in nitrogen atmosphere, 200 g of 1-indanone and 855 g of phenol; then, 59.4 g of sulfuric acid followed by 16.1 g of 3-mercaptopropionic acid were added slowly dropwise at temperatures equal to or below 40° C. After the dropwise addition, the temperature was raised and the mixture was allowed to react at 55° C. for 20 hours. Then, 300 g of ethyl acetate and 50.4 g of a 48% by weight sodium hydroxide aqueous solution were added until neutral, and the precipitated crystals were filtered, to give 224 g of a crude product. The crude product was dissolved in 1450 g of ethyl acetate and was washed with 500 g of a 5% by weight ammonium acetate aqueous solution until the organic layer exhibited a pH of 4 to 5. Then, 50 g of anhydrous magnesium sulfate was added to the separated organic layer, and the mixture was dried. Ethyl acetate in the filtrate was removed by evaporation, and when crystals started to precipitate, 400 g of toluene was added thereto to crystallize. These crystals were collected by filtration and washed by dispersing in toluene, and were then dried under reduced pressure at 40° C., to give 135 g of white crystals (yield: 30%). The white crystals had a melting point of 215° C., and various analyses confirmed that the white crystals were Compound P-1, the target compound.

Results of Analyses (1) $^1$H-NMR Chemical Shift: (ppm) 8.21 (s: 2H), 7.29-7.23 (m: 1H), 7.20-7.13 (m: 2H), 7.05-7.00 (m: 1H), 6.97 (d: 4H), 6.72 (d: 4H), 2.81 (t: 2H), 2.72 (t: 2H)

(2) IR Absorption (cm$^{-1}$) 3300, 3066, 3021, 2965, 2942, 2912, 2861, 2861, 2844, 1610, 1595, 1508, 1469, 1457, 1437, 1362, 1312, 1296, 1238, 1216, 1176, 1158, 1135, 1113, 1087, 1039, 1011, 966, 937, 899, 855, 825, 772, 754, 724, 675

Step 2

Producing Compound a-1 (Epoxy Compound (A) Represented by the Above General Formula (I))

[Formula 22]

To a 2 L four-neck flask equipped with a stirrer, a nitrogen inlet, a reflux condenser, and a thermometer were put, in nitrogen atmosphere, 29.2 g of Compound P-1 being the bisphenol compound (2) obtained in Step 1 and 142 g of epichlorohydrin; then, 0.412 g of benzyltriethylammonium chloride was added thereto and the mixture was stirred at 74° C. for 14 hours. Then, the temperature was dropped to 60° C., and 16.1 g of a 48% by weight sodium hydroxide aqueous solution was added dropwise under a reduced pressure of 13000 Pa, and the mixture was stirred for 2.5 hours while returning, back into the system, epichlorohydrin which formed an azeotropic mixture with water. When epichlorohydrin was no longer in an azeotropic state with water, the temperature was gradually raised while reducing the pressure, and epichlorohydrin was removed by evaporation at 120° C. for 2 hours. After returning the pressure to normal atmospheric pressure, 205 g of toluene was added, and washing with water was performed three times. To the organic layer obtained by oil/water separation were added 3.99 g of a 48% by weight sodium hydroxide aqueous solution, 0.412 g of benzyltriethylammonium chloride, and 0.870 g of water, and the mixture was stirred at 80° C. for 2.5 hours. The mixture was then cooled to room temperature, and 0.692 g of a 10% by weight sodium dihydrogen phosphate aqueous solution was added until neutral, and washing with water was performed three times. The organic layer obtained by oil/water separation was filtered with Celite and the solvent was removed by evaporation, to give 36.6 g of a viscous, light-yellow substance (yield: 92%; epoxy equivalent: 212). Various analyses confirmed that the viscous, light-yellow substance was Compound a-1, the target compound.

Results of Analyses (1) $^1$H-NMR Chemical Shift: (ppm) 7.30-7.26 (m: 1H), 7.22-7.16 (m: 2H), 7.07 (d: 4H), 7.05-7.01 (m: 1H), 6.87 (d: 4H), 4.31 (d: 1H), 4.28 (d: 1H), 3.87 (d: 1H), 3.84 (d: 1H), 3.32-3.27 (m: 2H), 2.89 (t: 2H), 2.85 (t: 2H), 2.79-2.71 (m: 4H)

(2) IR Absorption (cm$^{-1}$) 3061, 3036, 3001, 2928, 2875, 2844, 1712, 1606, 1579, 1508, 1472, 1456, 1432, 1414, 1347, 1295, 1246, 1183, 1158, 1133, 1118, 1086, 1032, 970, 915, 861, 828, 771, 756, 730

Step 3

Producing Compound w-1 (Epoxy Adduct (W))

In a reactor were put 149 g of Compound a-1 obtained in Step 2 above as the epoxy compound (A), 37.3 g of acrylic acid (also referred to hereinafter as Compound b) as the unsaturated monobasic acid (B), 0.398 g of 2,6-di-t-butyl-p-cresol, 0.909 g of tetrabutylammonium chloride, and 54.5 g of propylene glycol-1-monomethyl ether-2-acetate (also referred to hereinafter as PGMAc), and the mixture was stirred at 90° C. for 1 hour, at 105° C. for 1 hour, and at 120°

Compound a-1

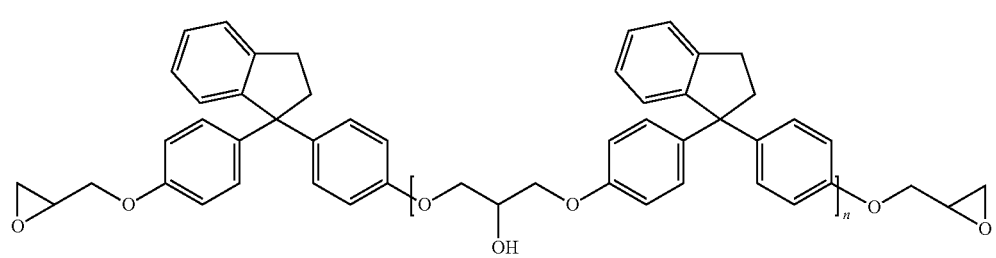

C. for 17 hours, to give the target compound as a PGMAc solution. Various analyses confirmed that this was Compound w-1 (acid value (solids content): 1.06 mgKOH/g), the target compound. The Compound w-1 had a structure in which addition was carried out at a ratio wherein the number of carboxyl groups in the Compound b was 1.0 with respect to one epoxy group in the Compound a-1.

IR Absorption (cm$^{-1}$) 3449, 3064, 3036, 2944, 2877, 2841, 1725, 1634, 1608, 1580, 1508, 1472, 1457, 1408, 1373, 1295, 1247, 1183, 1130, 1117, 1063, 1048, 1011, 984, 938, 900, 827, 810, 771, 756, 731, 667

Example 1-2

Step 1

Producing 1,1-bis(4-hydroxyphenyl)-3-phenylindan (Bisphenol Compound (2); Also Referred to Hereinafter as P-2)

[Formula 23]

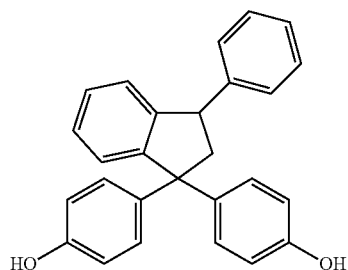

Compound P-2

To a 1 L four-neck flask equipped with a stirrer, a nitrogen inlet, a reflux condenser, and a thermometer were put, in nitrogen atmosphere, 93.6 g of 3-phenyl-1-indanone, 254 g of phenol, and 2.4 g of 3-mercaptopropionic acid; then, 17.7 g of sulfuric acid was added thereto dropwise. After allowing the mixture to react at 60° C. for 10 hours, 300 g of water and 800 g of ethyl acetate were added. Then, a 48% sodium hydroxide aqueous solution was added thereto until neutral, and washing was performed using 300 g of a 20% sodium chloride solution. Ethyl acetate in the organic layer was removed by evaporation and the precipitation obtained by adding 200 g of toluene was collected, to give 135 g of a crude product. The crude product was crystallized using a mixed solvent of ethyl acetate and toluene, to give 110 g of white crystals (yield: 65%). Various analyses confirmed that the white crystals were Compound P-2, the target compound.

Results of Analyses (1) $^1$H-NMR Chemical Shift: (ppm) 9.32 (s: 1H), 9.28 (s: 1H), 7.33 (t: 2H), 7.29-7.19 (m: 4H), 7.19-7.10 (m: 1H), 7.04 (d: 1H), 6.99 (d: 2H), 6.92 (d: 2H), 6.74 (d: 1H), 6.71-6.64 (m: 4H), 4.15-4.08 (m: 1H), 3.17-3.09 (m: 1H), 2.69-2.60 (m: 1H)

(2) IR Absorption (cm$^{-1}$) 3276, 3062, 3025, 2960, 2930, 2878, 1612, 1596, 1559, 1506, 1469, 1450, 1375, 1350, 1308, 1231, 1180, 1150, 1113, 1073, 1012, 912, 836, 763, 754, 733

Step 2

Producing Compound a-2 (Epoxy Compound (A) Represented by the Above General Formula (I))

[Formula 24]

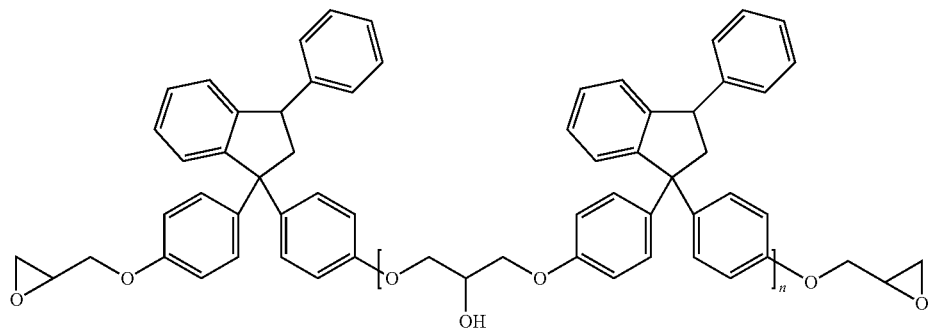

Compound a-2

To a 1 L four-neck flask equipped with a stirrer, a nitrogen inlet, a reflux condenser, and a thermometer were put, in nitrogen atmosphere, 100 g of Compound P-2 being the bisphenol compound (2) and 392 g of epichlorohydrin; then, 1.20 g of benzyltriethylammonium chloride was added, and the mixture was stirred at 78° C. for 14 hours. Then, the temperature was dropped to 60° C., and 44.3 g of a 24% by weight sodium hydroxide aqueous solution was added dropwise under a reduced pressure of 13000 Pa, and the mixture was stirred for 30 minutes while returning, back into the system, epichlorohydrin which formed an azeotropic mixture. Epichlorohydrin and water were removed by evaporation, 400 g of toluene was added, and washing with water was performed. To this solution, 2.2 g of a 24% by weight sodium hydroxide aqueous solution was added dropwise, and the mixture was stirred at 80° C. for 2 hours. Then, the mixture was cooled to room temperature, neutralized with a 3% by weight sodium dihydrogen phosphate aqueous solution, and washed with water. The solvent was removed by evaporation, to give 103 g of a yellow solid (yield: 79%; epoxy equivalent: 254). Various analyses confirmed that the yellow crystals were Compound a-2, the target compound.

Results of Analyses (1) $^1$H-NMR Chemical Shift: (ppm) 7.35 (t: 2H), 7.28 (d: 3H), 7.23-7.15 (m: 2H), 7.15-7.08 (m: 4H), 7.06 (d: 1H), 6.92 (d: 1H), 6.88-6.80 (m: 4H), 4.25-4.12 (m: 3H), 4.0-3.91 (m: 2H), 3.39-3.31 (m: 2H), 3.20-3.11 (m: 1H), 2.94-2.83 (m: 3H), 2.77-2.73 (m: 2H)

(2) IR Absorption (cm$^{-1}$) 3549, 3028, 2925, 2871, 1699, 1606, 1579, 1541, 1503, 1471, 1455, 1396, 1295, 1246, 1183, 1134, 1036, 914, 830, 757, 702

Example 1-3

Step 1

Producing 1,1-bis(4-hydroxyphenyl)-3,5-diphenylindan (Bisphenol Compound (2); Also Referred to Hereinafter as P-3)

[Formula 25]

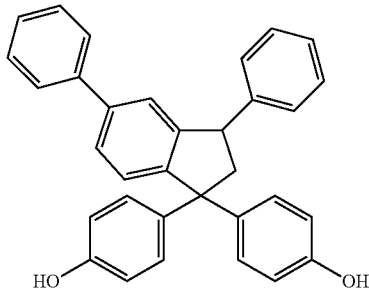

Compound P-3

To a 1 L four-neck flask equipped with a stirrer, a nitrogen inlet, a reflux condenser, and a thermometer were put, in nitrogen atmosphere, 92.8 g of 3,5-diphenyl-1-indanone, 184 g of phenol, and 1.73 g of 3-mercaptopropionic acid; then, 12.8 g of sulfuric acid was added dropwise. After allowing the mixture to react at 60° C. for 15 hours, 300 g of water and 800 g of ethyl acetate were added. Then, a 48% sodium hydroxide aqueous solution was added thereto until neutral, and washing was performed using 300 g of a 20% sodium chloride solution. Ethyl acetate in the organic layer was removed by evaporation and the precipitation obtained by adding 200 g of toluene was collected, to give 112.4 g of a crude product. The crude product was crystallized using a mixed solvent of ethyl acetate and toluene, to give 61.7 g of white crystals (yield: 42%). Various analyses confirmed that the white crystals were Compound P-3, the target compound.

Results of Analyses (1) $^1$H-NMR Chemical Shift: (ppm) 9.32 (s: 1H), 9.28 (s: 1H), 7.55-7.48 (m: 3H), 7.41-7.25 (m: 8H), 7.14 (d: 1H), 7.06 (d: 2H), 6.96-6.93 (m: 3H), 6.70 (t: 4H), 4.22-4.15 (m: 1H), 3.23-3.15 (m: 1H), 2.68 (t: 1H)

(2) IR Absorption (cm$^{-1}$) 3592, 3293, 3025, 2955, 2930, 2876, 1608, 1595, 1509, 1474, 1441, 1368, 1350, 1298, 1252, 1236, 1177, 1112, 1012, 901, 864, 831, 765, 703

Step 2

Producing Compound a-3 (Epoxy Compound (A) Represented by the Above General Formula (I))

[Formula 26]

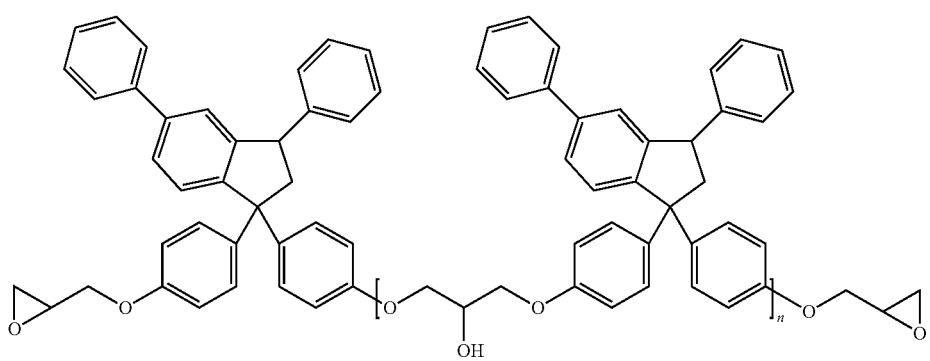

Compound a-3

To a 1 L four-neck flask equipped with a stirrer, a nitrogen inlet, a reflux condenser, and a thermometer were put, in nitrogen atmosphere, 55.0 g of Compound P-3 being the bisphenol compound (2) and 179 g of epichlorohydrin; then, 0.28 g of benzyltriethylammonium chloride was added thereto, and the mixture was stirred at 78° C. for 14 hours. Then, the temperature was dropped to 60° C., and 28.1 g of a 48% by weight potassium hydroxide aqueous solution was added dropwise under a reduced pressure of 13000 Pa, and the mixture was stirred for 2 hours while returning, back into the system, epichlorohydrin which formed an azeotropic mixture. Epichlorohydrin and water were removed by evaporation, 400 g of toluene was added, and washing with water was performed. To this toluene solution, 4.0 g of a 48% by weight potassium hydroxide aqueous solution was added, and the mixture was stirred at 80° C. for 2 hours. Then, the mixture was cooled to room temperature, neutralized with a 5% by weight sodium dihydrogen phosphate aqueous solution, and washed with water. The solvent was removed by evaporation, and the resulting viscous liquid was crystallized using a mixed solvent of toluene and 2-propanol, to give 44.2 g of yellow-white crystals (yield: 76%; epoxy equivalent: 292). Various analyses confirmed that the yellow-white crystals were the target compound a-3.

Results of Analyses (1) $^1$H-NMR Chemical Shift: (ppm) 7.52-7.45 (m: 3H), 7.40-7.24 (m: 8H), 7.20-7.12 (m: 6H), 6.89-6.83 (m: 4H), 4.26-4.18 (m: 3H), 4.00-3.94 (m: 2H), 3.40-3.33 (m: 2H), 3.23-3.17 (m: 1H), 2.94-2.86 (m: 3H), 2.79-2.74 (m: 2H)

(2) IR Absorption (cm$^{-1}$) 3466, 3060, 3029, 2936, 2871, 1606, 1581, 1508, 1476, 1454, 1411, 1347, 1298, 1247, 1182, 1076, 1037, 968, 915, 831, 764, 702

Usage Example 1

3.5 g of the epoxy compound a-1, 1.5 g of PGMAc, 2.74 g of methyltetrahydrophthalic anhydride (also referred to hereinafter as MTHPA), and 0.06 g of 2-ethyl-4-methylimidazole (also referred to hereinafter as 2E4MZ) were mixed, to prepare an epoxy resin composition of Usage Example 1. Then, 3 g of the epoxy resin composition was applied evenly on a glass plate at a diameter of 7 cm, and the composition was cured by heating at 80° C. for 60 minutes, and then at 150° C. for 120 minutes, to obtain a cured product. The obtained cured product was immersed in an 80° C. hot water bath for 60 minutes, and the rate of increase in mass (%) was determined as "water absorption rate". The results are shown in Table 1.

Comparative Usage Example 1

An epoxy resin composition of Comparative Usage Example 1 was prepared by mixing 3.5 g of 1,1-bis[4-(2,3-epoxypropyloxy)phenyl]-1-(4-biphenylyl)-1-cyclohexyl methane (also referred to hereinafter as Compound E-BC), 1.5 g of PGMAc, 2.08 g of MTHPA, and 0.06 g of 2E4MZ. Then, 3 g of the epoxy resin composition was applied evenly on a glass plate at a diameter of 7 cm, and the composition was cured by heating at 80° C. for 60 minutes, and then at 150° C. for 120 minutes, to obtain a cured product. The obtained cured product was immersed in an 80° C. hot water bath for 60 minutes, and the rate of increase in mass (%) was determined as "water absorption rate". The results are shown in Table 1.

Comparative Usage Example 2

An epoxy resin composition of Comparative Usage Example 2 was prepared by mixing 3.5 g of bisphenol A diglycidyl ether (EP-4100E manufactured by ADEKA Corporation; also referred to hereinafter as BisADGE), 1.5 g of PGMAc, 3.13 g of MTHPA, and 0.06 g of 2E4MZ. Then, 3 g of the epoxy resin composition was applied evenly on a glass plate at a diameter of 7 cm, and the composition was cured by heating at 80° C. for 60 minutes, and then at 150° C. for 120 minutes, to obtain a cured product. The obtained cured product was immersed in an 80° C. hot water bath for 60 minutes, and the rate of increase in mass (%) was determined as "water absorption rate". The results are shown in Table 1.

TABLE 1

| | | Usage Example | Comparative Usage Example | |
|---|---|---|---|---|
| | | 1 | 1 | 2 |
| Epoxy Compound | Compound a-1 | 3.5 | | |
| | Compound E-BC | | 3.5 | |
| | Compound BisADGE | | | 3.5 |
| PGMAc | | 1.5 | 1.5 | 1.5 |
| MTHPA | | 2.74 | 2.08 | 3.13 |
| 2E4MZ | | 0.06 | 0.06 | 0.06 |
| Water Absorption Rate (%) | | 0.44 | 0.47 | 0.54 |

Example 2-1

Producing Alkali-Developable Resin Composition No. 1

In a reactor were put 30.0 g of Compound a-1 obtained in Step 2 of Example 1-1 as the epoxy compound (A), 7.52 g of Compound b as the unsaturated monobasic acid (B), 0.080 g of 2,6-di-t-butyl-p-cresol, 0.183 g of tetrabutylammonium chloride, and 11.0 g of PGMAc, and the mixture was stirred at 90° C. for 1 hour, at 105° C. for 1 hour, and at 120° C. for 17 hours. The mixture was cooled to room temperature, 8.11 g of succinic anhydride (also referred to hereinafter as Compound c-1) as the polybasic acid anhydride (C), 0.427 g of tetrabutylammonium chloride, and 11.1 g of PGMAc were added, and the mixture was stirred at 100° C. for 5 hours. Further, 12.0 g of a-1 obtained in Step 2 of Example 1 as the epoxy compound (D), 0.080 g of 2,6-di-t-butyl-p-cresol, and 0.600 g of PGMAc were added, and the mixture was stirred at 90° C. for 90 minutes and at 120° C. for 5 hours. Then, 24.0 g of PGMAc was added, to give an alkali-developable resin composition No. 1, the target composition, as a PGMAc solution thereof (Mw: 4900; Mn: 2250; acid value (solids content): 47 mgKOH/g). The obtained alkali-developable resin composition No. 1 contained 44.4% by mass of the photopolymerizable unsaturated compound (Y), the reaction product.

Note that the photopolymerizable unsaturated compound (Y) contained by the alkali-developable resin composition No. 1 was obtained by causing reaction between the epoxy adduct (W) and Compounds c-1 and a-1 at a ratio wherein, with respect to one hydroxyl group in the epoxy adduct (W) having a structure in which the Compound b as the component (B) was added to the Compound a-1 as the component (A), the number of acid anhydride structures in the Compound c-1 as the component (C) was 0.8 and the number of epoxy groups in the Compound a-1 as the component (D) was 0.4. Further, the epoxy adduct (W) had a structure in which addition was carried out at a ratio wherein the number of carboxyl groups in the Compound b was 1.0 with respect to one epoxy group in the Compound a-1.

Example 2-2

Producing Alkali-Developable Resin Composition No. 2

In a reactor were put 30.0 g of Compound a-1 obtained in Step 2 of Example 1-1 as the epoxy compound (A), 7.52 g of Compound b as the unsaturated monobasic acid (B), 0.104 g of 2,6-di-t-butyl-p-cresol, 0.183 g of tetrabutylammonium chloride, and 11.0 g of PGMAc, and the mixture was stirred at 90° C. for 1 hour, at 105° C. for 1 hour, and at 120° C. for 17 hours. The mixture was cooled to room temperature, 9.24 g of 3,3',4,4'-biphenyltetracarboxylic dianhydride (also referred to hereinafter as Compound c-2) and 0.154 g of 1,2,3,6-tetrahydrophthalic anhydride (also referred to hereinafter as Compound c-3) as the polybasic acid anhydride (C), 0.427 g of tetrabutylammonium chloride, and 12.1 g of PGMAc were added, and the mixture was stirred at 120° C. for 5 hours, at 90° C. for 1 hour, at 60° C. for 2 hours, and at 40° C. for 3 hours. Then, 17.5 g of PGMAc was added, to give an alkali-developable resin composition No. 2, the target composition, as a PGMAc solution thereof (Mw: 6370; Mn: 2570; acid value (solids content): 94 mgKOH/g).

The obtained alkali-developable resin composition No. 2 contained 44.5% by mass of the photopolymerizable unsaturated compound (X), the reaction product.

Note that the photopolymerizable unsaturated compound (X) contained by the alkali-developable resin composition No. 2 was obtained by causing esterification between the epoxy adduct (W) and Compounds c-2 and c-3 at a ratio wherein, with respect to one hydroxyl group in the epoxy adduct (W) having a structure in which the Compound b as the component (B) was added to the Compound a-1 as the component (A), the number of acid anhydride structures in the Compound c-2 as the component (C) was 0.62 and the number of acid anhydride structures in the Compound c-3 as the component (C) was 0.01. Further, the epoxy adduct (W) had a structure in which addition was carried out at a ratio wherein the number of carboxyl groups in the Compound b was 1.0 with respect to one epoxy group in the Compound a-1.

Example 2-3

Producing Alkali-Developable Resin Composition No. 3

In a reactor were put 30.0 g of Compound a-1 obtained in Step 2 of Example 1-1 as the epoxy compound (A), 7.52 g of Compound b as the unsaturated monobasic acid (B), 0.104 g of 2,6-di-t-butyl-p-cresol, 0.183 g of tetrabutylammonium chloride, and 11.0 g of PGMAc, and the mixture was stirred at 90° C. for 1 hour, at 105° C. for 1 hour, and at 120° C. for 17 hours. The mixture was cooled to room temperature, 7.75 g of Compound c-2 and 1.69 g of Compound c-3 as the polybasic acid anhydride (C), 0.427 g of tetrabutylammonium chloride, and 12.1 g of PGMAc were added, and the mixture was stirred at 120° C. for 5 hours, at 90° C. for 1 hour, at 60° C. for 2 hours, and at 40° C. for 3 hours. Then, 17.5 g of PGMAc was added, to give an alkali-developable resin composition No. 3, the target composition, as a PGMAc solution thereof (Mw: 4590; Mn: 2120; acid value (solids content): 93 mgKOH/g). The obtained alkali-developable resin composition No. 3 contained 44.5% by mass of the photopolymerizable unsaturated compound (X), the reaction product.

Note that the photopolymerizable unsaturated compound (X) contained by the alkali-developable resin composition No. 3 was obtained by causing esterification between the epoxy adduct (W) and Compounds c-2 and c-3 at a ratio wherein, with respect to one hydroxyl group in the epoxy adduct (W) having a structure in which the Compound b as the component (B) was added to the Compound a-1 as the component (A), the number of acid anhydride structures in the Compound c-2 as the component (C) was 0.52 and the number of acid anhydride structures in the Compound c-3 as the component (C) was 0.11. Further, the epoxy adduct (W) had a structure in which addition was carried out at a ratio wherein the number of carboxyl groups in the Compound b was 1.0 with respect to one epoxy group in the Compound a-1.

Example 2-4

Producing Alkali-Developable Resin Composition No. 4

In a reactor were put 30.0 g of Compound a-1 obtained in Step 2 of Example 1-1 as the epoxy compound (A), 7.52 g of Compound b as the unsaturated monobasic acid (B), 0.080 g of 2,6-di-t-butyl-p-cresol, 0.183 g of tetrabutylammonium chloride, and 11.0 g of PGMAc, and the mixture was stirred at 90° C. for 1 hour, at 105° C. for 1 hour, and at 120° C. for 17 hours. The mixture was cooled to room temperature, 7.10 g of Compound c-1 and 1.56 g of hexahydrophthalic anhydride (also referred to hereinafter as Compound c-4) as the polybasic acid anhydride (C), 0.427 g of tetrabutylammonium chloride, and 11.5 g of PGMAc were added, and the mixture was stirred at 100° C. for 5 hours. Then, the mixture was cooled to room temperature, 15.9 g of Compound a-1 obtained in Step 2 of Example 1 as the epoxy compound (D) and 0.087 g of 2,6-di-t-butyl-p-cresol were added, and the mixture was stirred at 90° C. for 90 minutes, at 120° C. for 4 hours, and at 100° C. for 7 hours. Further, 3.84 g of Compound c-3 as the polybasic acid anhydride (E) was added, the mixture was stirred at 100° C. for 3 hours, and then 25.3 g of PGMAc was added, to give an alkali-developable resin composition No. 4, the target composition, as a PGMAc solution thereof (Mw: 6500; Mn: 3000; acid value (solids content): 58 mgKOH/g). The obtained alkali-developable resin composition No. 4 contained 44.4% by mass of the photopolymerizable unsaturated compound (Z), the reaction product.

Note that the photopolymerizable unsaturated compound (Z) contained by the alkali-developable resin composition No. 4 was obtained by causing reaction among the epoxy adduct (W) and Compounds c-1, c-4, a-1, and c-3 at a ratio wherein, with respect to one hydroxyl group in the epoxy adduct (W) having a structure in which the Compound b as the component (B) was added to the Compound a-1 as the component (A), the number of acid anhydride structures in the Compound c-1 as the component (C) was 0.7, the number of acid anhydride structures in the Compound c-4 was 0.1, the number of epoxy groups in the Compound a-1 as the component (D) was 0.53, and the number of acid anhydride structures in the Compound c-3 as the component (E) was 0.28. Further, the epoxy adduct (W) had a structure in which addition was carried out at a ratio wherein the number of carboxyl groups in the Compound b was 1.0 with respect to one epoxy group in the Compound a-1.

Example 2-5

Producing Alkali-Developable Resin Composition No. 5

In a reactor were put 18.5 g of Compound a-2 obtained in Step 2 of Example 1-2 as the epoxy compound (A), 5.37 g of Compound b as the unsaturated monobasic acid (B), 0.07 g of 2,6-di-tert-butyl-p-cresol, 0.132 g of benzyltriethylammonium chloride, and 15.9 g of PGMAc, and the mixture was stirred at 120° C. for 16 hours. The mixture was cooled to room temperature, 5.58 g of Compound c-2 and 1.90 g of Compound c-3 as the polybasic acid anhydride (C), as well as 0.132 g of benzyltriethylammonium chloride and 9.74 g of PGMAc, were put in, and the mixture was stirred at 120° C. for 5 hours, at 90° C. for 1 hour, at 60° C. for 2 hours, and at 40° C. for 3 hours. Then, 12.7 g of PGMAc was added, to give an alkali-developable resin composition No. 5, the target composition, as a PGMAc solution thereof (Mw: 4200; Mn: 2100; acid value (solids content): 97 mgKOH/g). The obtained alkali-developable resin composition No. 5 contained 44.6% by weight of the photopolymerizable unsaturated compound (Y), the reaction product.

Note that the photopolymerizable unsaturated compound (Y) contained by the alkali-developable resin composition No. 5 was obtained by causing reaction between the epoxy adduct (W) and Compounds c-2 and c-3 at a ratio wherein, with respect to one hydroxyl group in the epoxy adduct (W) having a structure in which the Compound b as the component (B) was added to the Compound a-2 as the component (A), the number of acid anhydride structures in the Compound c-2 as the component (C) was 0.52 and the number of acid anhydride structures in the Compound c-3 as the component (C) was 0.17. Further, the epoxy adduct (W) had a structure in which addition was carried out at a ratio wherein the number of carboxyl groups in the Compound b was 1.0 with respect to one epoxy group in the Compound a-2.

Example 2-6

Producing Alkali-Developable Resin Composition No. 6

In a reactor were put 13.9 g of Compound a-2 obtained in Step 2 of Example 1-2 as the epoxy compound (A), 4.03 g of Compound b as the unsaturated monobasic acid (B), 0.05 g of 2,6-di-tert-butyl-p-cresol, 0.100 g of benzyltriethylammonium chloride, and 11.9 g of PGMAc, and the mixture was stirred at 120° C. for 16 hours. The mixture was cooled to room temperature, 4.39 g of Compound c-1 as the polybasic acid anhydride (C), as well as 0.180 g of benzyltriethylammonium chloride and 6.30 g of PGMAc, were put in, and the mixture was stirred at 100° C. for 5 hours. The mixture was cooled to room temperature, 5.55 g of Compound a-2 obtained in Step 2 of Example 1-2 as the epoxy compound (D) and 0.05 g of 2,6-di-tert-butyl-p-cresol were added, and the mixture was stirred at 120° C. for 8 hours. Then, 15.8 g of PGMAc was added, to give an alkali-developable resin composition No. 6, the target composition, as a PGMAc solution thereof (Mw: 4400; Mn: 2000; acid value (solids content): 49 mgKOH/g). The obtained alkali-developable resin composition No. 6 contained 44.8% by weight of the photopolymerizable unsaturated compound (Y), the reaction product.

Note that the photopolymerizable unsaturated compound (Y) contained by the alkali-developable resin composition No. 6 was obtained by causing reaction between the epoxy adduct (W) and Compounds c-1 and a-2 at a ratio wherein, with respect to one hydroxyl group in the epoxy adduct (W) having a structure in which the Compound b as the component (B) was added to the Compound a-2 as the component (A), the number of acid anhydride structures in the Compound c-1 as the component (C) was 0.80 and the number of epoxy groups in the Compound a-2 as the component (D) was 0.4. Further, the epoxy adduct (W) had a structure in which addition was carried out at a ratio wherein the number of carboxyl groups in the Compound b was 1.0 with respect to one epoxy group in the Compound a-2.

Example 2-7

Producing Alkali-Developable Resin Composition No. 7

In a reactor were put 30.0 g of Compound a-3 obtained in Step 2 of Example 1-3 as the epoxy compound (A), 7.56 g of Compound b, 0.10 g of 2,6-di-tert-butyl-p-cresol, 0.186 g of benzyltriethylammonium chloride and 37.3 g of PGMAc, and the mixture was stirred at 120° C. for 20 hours. The mixture was cooled to room temperature, 6.36 g of Compound c-2 and 5.49 g of Compound c-3 as the polybasic acid anhydride (C), 0.434 g of benzyltriethylammonium chloride, and 2.86 g of PGMAc were put in, and the mixture was stirred at 120° C. for 5 hours, at 90° C. for 1 hour, at 60° C. for 2 hours, and at 40° C. for 3 hours. Then, the mixture was diluted with 51.6 g of PGMAc, to give an alkali-developable resin composition No. 7, the target composition, as a PGMAc solution thereof (Mw: 2820; Mn: 1950; acid value (solids content): 96 mgKOH/g). The obtained alkali-developable resin composition No. 7 contained 35.6% by weight of the photopolymerizable unsaturated compound (Y), the reaction product.

Note that the photopolymerizable unsaturated compound (Y) contained by the alkali-developable resin composition No. 7 was obtained by causing reaction between the epoxy adduct (W) and Compounds c-2 and c-3 at a ratio wherein, with respect to one hydroxyl group in the epoxy adduct (W) having a structure in which the Compound b as the component (B) was added to the Compound a-3 as the component (A), the number of acid anhydride structures in the Compound c-2 as the component (C) was 0.42 and the number of acid anhydride structures in the Compound c-3 as the component (C) was 0.35. Further, the epoxy adduct (W) had a structure in which addition was carried out at a ratio wherein the number of carboxyl groups in the Compound b was 1.0 with respect to one epoxy group in the Compound a-3.

Comparative Example 1-1

Producing Comparative Alkali-Developable Resin Composition No. 1

In a reactor were put 1695 g of Compound E-BC, 443 g of Compound b, 6 g of 2,6-di-t-butyl-p-cresol, 11 g of tetrabutylammonium chloride, and 1425 g of PGMAc, and the mixture was stirred at 90° C. for 1 hour, at 100° C. for 1 hour, at 110° C. for 1 hour, and at 120° C. for 16 hours. The mixture was cooled to room temperature, 718 g of PGMAc, 482 g of Compound c-1, and 25 g of tetrabutylammonium chloride were added, and the mixture was stirred at 100° C. for 5 hours. Further, 508 g of Compound E-BC and 218 g of PGMAc were added, and the mixture was stirred at 90° C. for 90 minutes and at 120° C. for 11 hours. Then, 1463 g of PGMAc was added, to give a comparative alkali-developable resin composition No. 1, the target composition, as a PGMAc solution thereof (Mw: 4200; Mn: 2200; acid value (solids content): 53 mgKOH/g).

Comparative Example 1-2

Producing Comparative Alkali-Developable Resin Composition No. 2

In a reactor were put 390 g of Compound E-BC, 71.1 g of Compound b, 1.34 g of 2,6-di-t-butyl-p-cresol, 1.75 g of tetrabutylammonium chloride, and 108 g of PGMAc, and the mixture was stirred at 90° C. for 1 hour, at 100° C. for 1 hour, at 110° C. for 1 hour, and at 120° C. for 17 hours. The mixture was cooled to room temperature, 59.2 g of Compound c-2, 45.2 g of Compound c-3, 4.08 g of tetrabutylammonium chloride, and 137 g of PGMAc were added, and the mixture was stirred at 120° C. for 5 hours, at 90° C. for 1 hour, at 60° C. for 2 hours, and at 40° C. for 3 hours. Then, 203 g of PGMAc was added, to give a comparative alkali-developable resin composition No. 2, the target composition, as a PGMAc solution thereof (Mw: 3700; Mn: 2000; acid value (solids content): 91 mgKOH/g).

Comparative Example 1-3

Producing Comparative Alkali-Developable Resin Composition No. 3

In a reactor were put 75.0 g of 9,9-bis[4-(2,3-epoxypropyloxy)phenyl]fluorene, 23.8 g of Compound b, 0.273 g of 2,6-di-t-butyl-p-cresol, 0.585 g of tetrabutylammonium chloride, and 65.9 g of PGMAc, and the mixture was stirred at 90° C. for 1 hour, at 100° C. for 1 hour, at 110° C. for 1 hour, and at 120° C. for 14 hours. The mixture was cooled to room temperature, 25.9 g of Compound c-1, 0.427 g of tetrabutylammonium chloride, and 1.37 g of PGMAc were added, and the mixture was stirred at 100° C. for 5 hours. Further, 30.0 g of 9,9-bis[4-(2,3-epoxypropyloxy)phenyl]fluorene, 0.269 g of 2,6-di-t-butyl-p-cresol, and 1.50 g of PGMAc were added, and the mixture was stirred at 90° C. for 90 minutes and at 120° C. for 4 hours. Then, 93.4 g of PGMAc was added, to give a comparative alkali-developable resin composition No. 3, the target composition, as a PGMAc solution thereof (Mw: 4190; Mn: 2170; acid value (solids content): 52 mgKOH/g).

Comparative Example 1-4

Producing Comparative Alkali-Developable Resin Composition No. 4

In a reactor were put 184 g of 9,9-bis[4-(2,3-epoxypropyloxy)phenyl]fluorene, 58.0 g of Compound b, 0.26 g of 2,6-di-t-butyl-p-cresol, 0.11 g of tetrabutylammonium chloride, and 23.0 g of PGMAc, and the mixture was stirred at 120° C. for 16 hours. The mixture was cooled to room temperature, 35 g of PGMAc, 59.0 g of Compound c-2, and 0.24 g of tetra-n-butylammonium bromide were added, and the mixture was stirred at 120° C. for 4 hours. Further, 20.0 g of Compound c-3 was added, and the mixture was stirred at 120° C. for 4 hours, at 100° C. for 3 hours, at 80° C. for 4 hours, at 60° C. for 6 hours, and at 40° C. for 11 hours. Then, 90 g of PGMAc was added, to give a comparative alkali-developable resin composition No. 4, the target composition, as a PGMAc solution thereof (Mw: 5000; Mn: 2100; acid value (solids content): 93 mgKOH/g).

Comparative Example 1-5

Producing Comparative Alkali-Developable Resin Composition No. 5

In a reactor were put 154 g of BisADGE, 59.0 g of Compound b, 0.26 g of 2,6-di-t-butyl-p-cresol, 0.11 g of tetrabutylammonium chloride, and 23.0 g of PGMAc, and the mixture was stirred at 120° C. for 16 hours. The mixture was cooled to room temperature, 365 g of PGMAc, 67.0 g of Compound c-2, and 0.24 g of tetra-n-butylammonium bromide were added, and the mixture was stirred at 120° C. for 4 hours, at 100° C. for 3 hours, at 80° C. for 4 hours, at 60° C. for 6 hours, and at 40° C. for 11 hours. Then, 90.0 g of PGMAc was added, to give a comparative alkali-developable resin composition No. 5, the target composition, as a PGMAc solution thereof (Mw: 7500; Mn: 2100; acid value (solids content): 91 mgKOH/g).

Examples 3-1 to 3-7 (Preparation of alkali-developable photosensitive resin compositions Nos. 1 to 7 respectively containing alkali-developable resin compositions Nos. 1 to 7 obtained in Examples 2-1 to 2-7) and Comparative Examples 2-1 to 2-5 (Preparation of comparative alkali-developable photosensitive resin compositions Nos. 1 to 5 respectively containing comparative alkali-developable resin compositions Nos. 1 to 5 obtained in Comparative Examples 1-1 to 1-5)

Respectively to 44 g of the alkali-developable resin compositions Nos. 1 to 7 obtained in Examples 2-1 to 2-7 and the comparative alkali-developable resin compositions Nos. 1 to 5 obtained in Comparative Examples 1-1 to 1-5, 6.3 g of trimethylolpropane triacrylate, 2.1 g of benzophenone as the photopolymerization initiator (F), and 78 g of PGMAc were added and were stirred well, to respectively give alkali-developable photosensitive resin compositions Nos. 1 to 7 and comparative alkali-developable photosensitive resin compositions Nos. 1 to 5.

The alkali-developable photosensitive resin compositions Nos. 1 to 7 prepared in Examples 3-1 to 3-7 and the comparative alkali-developable photosensitive resin compositions Nos. 1 to 5 prepared in Comparative Examples 2-1 to 2-5 were evaluated as follows.

Gamma-glycidoxypropylmethylethoxy silane was applied on a substrate by spin coating and dried well by spin drying. Each of the alkali-developable photosensitive resin compositions was applied thereon by spin coating (at 1300 rpm for 50 seconds) and dried. The coating layer was prebaked at 70° C. for 20 minutes, and a 5% polyvinyl alcohol solution was coated thereon to form an oxygen barrier film. After drying at 70° C. for 20 minutes, each coated substrate was exposed to light using an ultrahigh pressure mercury lamp, as the light source, through a prescribed mask. Then, the coating was developed by being immersed into a 2.5% sodium carbonate solution at 25° C. for 30 seconds and washed with water thoroughly. After washing and drying, the coating was baked at 230° C. for 1 hour to fix the pattern. The following evaluation was made for the patterns obtained. The results are shown in Table 2.

Sensitivity:

Compositions for which an exposure of 70 $mJ/cm^2$ was sufficient were rated "a", compositions for which an exposure of 70 $mJ/cm^2$ was insufficient and which were thus exposed at 100 $mJ/cm^2$ were rated "b", and compositions for which an exposure of 100 $mJ/cm^2$ was insufficient and which were thus exposed at 150 $mJ/cm^2$ were rated "c".

Resolution:

Upon exposure-and-development, compositions that succeeded in forming satisfactory patterns even at line widths of 8 μm or below were rated "A", compositions that succeeded in forming satisfactory patterns at a line width of 10 μm were rated "B", and compositions that succeeded in forming satisfactory patterns only at line widths of 30 μm or above were rated "C".

Adhesion:

Visual observation was made on whether the developed patterns showed any peeling, and compositions that showed no peeling at all in the patterns were rated ".", and compositions that showed any peeling in the patterns were rated "x".

TABLE 2

| Alkali-Developable Photosensitive Resin Composition | Comparative Alkali-Developable Photosensitive Resin Composition | Sensitivity | Resolution | Adhesion |
|---|---|---|---|---|
| No. 1 (Example 3-1) | | a | A | ○ |
| No. 2 (Example 3-2) | | a | A | ○ |
| No. 3 (Example 3-3) | | a | A | ○ |
| No. 4 (Example 3-4) | | a | A | ○ |
| No. 5 (Example 3-5) | | a | A | ○ |
| No. 6 (Example 3-6) | | a | A | ○ |
| No. 7 (Example 3-7) | | a | A | ○ |
| | No. 1 (Comparative Example 2-1) | b | B | ○ |
| | No. 2 (Comparative Example 2-2) | b | B | ○ |
| | No. 3 (Comparative Example 2-3) | c | C | x |
| | No. 4 (Comparative Example 2-4) | c | C | x |
| | No. 5 (Comparative Example 2-5) | c | C | x |

The alkali-developable photosensitive resin compositions Nos. 1 to 7 of Examples 3-1 to 3-7 were highly sensitive and had good resolution and adhesion.

In contrast, the comparative alkali-developable photosensitive resin compositions Nos. 1 to 5 of Comparative Examples 2-1 to 2-5 had low sensitivity and thus inevitably required a large amount of light exposure, and also had reduced resolution and unsatisfactory adhesion.

Examples 4-1 to 4-7 (Preparation of alkali-developable, colored photosensitive resin compositions Nos. 1 to 7 respectively containing alkali-developable photosensitive resin compositions Nos. 1 to 7 obtained in Examples 3-1 to 3-7) and Comparative Examples 3-1 to 3-5 (Preparation of comparative alkali-developable, colored photosensitive resin compositions Nos. 1 to respectively containing comparative alkali-developable photosensitive resin compositions Nos. 1 to 5 obtained in Comparative Examples 2-1 to 2-5)

Respectively to 44 g of the alkali-developable photosensitive resin compositions Nos. 1 to 7 obtained in Examples 3-1 to 3-7 and the comparative alkali-developable photosensitive resin compositions Nos. 1 to 5 obtained in Comparative Examples 2-1 to 2-5, 8.0 g of trimethylolpropane triacrylate, 1.8 g of 2,4,6-trimethylbenzoyldiphenylphosphine oxide as the photopolymerization initiator (F), 3.2 g of MA100 (carbon black manufactured by Mitsubishi Chemical Corp.) as the colorant (G), and 75 g of PGMAc were added and were stirred well, to respectively give alkali-developable, colored photosensitive resin compositions Nos. 1 to 7 and comparative alkali-developable, colored photosensitive resin compositions Nos. 1 to 5.

The alkali-developable, colored photosensitive resin compositions Nos. 1 to 7 prepared in the Examples 4-1 to 4-7 and the comparative alkali-developable, colored photosensitive resin compositions Nos. 1 to 5 prepared in the Comparative Examples 3-1 to 3-5 were evaluated in the same way as the above Examples 3-1 to 3-7. The results are shown in Table 3.

TABLE 3

| Alkali-Developable, Colored Photosensitive Resin Composition | Comparative Alkali-Developable, Colored Photosensitive Resin Composition | Sensitivity | Resolution | Adhesion |
|---|---|---|---|---|
| No. 1 (Example 4-1) | | a | A | ○ |
| No. 2 (Example 4-2) | | a | A | ○ |
| No. 3 (Example 4-3) | | a | A | ○ |
| No. 4 (Example 4-4) | | a | A | ○ |
| No. 5 (Example 4-5) | | a | A | ○ |
| No. 6 (Example 4-6) | | a | A | ○ |
| No. 7 (Example 4-7) | | a | A | ○ |
| | No. 1 (Comparative Example 3-1) | b | B | ○ |
| | No. 2 (Comparative Example 3-2) | b | B | ○ |
| | No. 3 (Comparative Example 3-3) | c | C | x |
| | No. 4 (Comparative Example 3-4) | c | C | x |
| | No. 5 (Comparative Example 3-5) | c | C | x |

The alkali-developable, colored photosensitive resin compositions Nos. 1 to 7 of Examples 4-1 to 4-7 were highly sensitive and had good resolution and adhesion.

In contrast, the comparative alkali-developable, colored photosensitive resin compositions Nos. 1 to 5 of Comparative Examples 3-1 to 3-5 had low sensitivity and thus inevitably required a large amount of light exposure, and also had reduced resolution and unsatisfactory adhesion.

INDUSTRIAL APPLICABILITY

The epoxy compound (A) of the present invention is useful as a material for an alkali-developable resin composition and an alkali-developable photosensitive resin composition. The alkali-developable resin composition and the alkali-developable photosensitive resin composition obtained by using the epoxy compound (A) have good sensitivity, resolution, and adhesion. Further, when mixed with a curing agent, the epoxy compound (A) of the present invention provides a thermosetting epoxy resin composition.

The invention claimed is:

1. An epoxy adduct having a structure formed by adding an unsaturated monobasic acid to an epoxy compound according to formula (I):

[Formula 1]

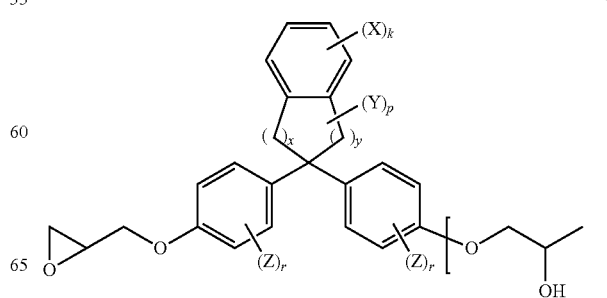

-continued

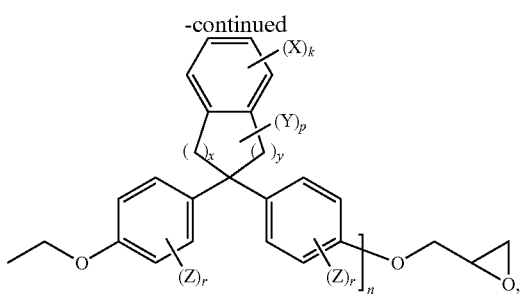

wherein
X, Y, and Z are each independently selected from the group consisting of:
an alkyl group having 1 to 10 carbon atoms and optionally having a methylene group in said alkyl group interrupted by an unsaturated bond, —O—, or —S—,
an alkyl group having 1 to 10 carbon atoms and having at least one hydrogen atom substituted with a halogen atom, and optionally having a methylene group in said alkyl group interrupted by an unsaturated bond, —O—, or —S—,
an aryl group having 6 to 20 carbon atoms and optionally having a methylene group in said aryl group interrupted by an unsaturated bond, —O—, or —S—,
an aryl group having 6 to 20 carbon atoms and having at least one hydrogen atom substituted with a halogen atom, and optionally having a methylene group in said aryl group interrupted by an unsaturated bond, —O—, or —S—,
an arylalkyl group having 7 to 20 carbon atoms and optionally having a methylene group in said arylalkyl group interrupted by an unsaturated bond, —O—, or —S—,
an arylalkyl group having 7 to 20 carbon atoms and having at least one hydrogen atom substituted with a halogen atom and optionally having a methylene group in said arylalkyl group interrupted by an unsaturated bond, —O—, or —S—,
a heterocyclic group having 2 to 20 carbon atoms,
a heterocyclic group having 2 to 20 carbon atoms and having at least one hydrogen atom substituted with a halogen atom; and
a halogen atom;
X is either independently selected from said group from which Y and Z are independently selected or one X forms a ring structure with the other X, and said ring structure is optionally an aromatic ring;

k, r, x and y are each independently a number of 0 to 4;
a sum of x and y is 2 to 4;
p is a number of 0 to 8;
n is 0 to 10; and
an optical isomer may exist when n is not 0.

2. An alkali-developable resin composition comprising a photopolymerizable unsaturated compound having a structure of a reaction product obtained by esterification between the epoxy adduct according to claim 1 and a polybasic acid anhydride.

3. An alkali-developable resin composition comprising a photopolymerizable unsaturated compound having a structure of a reaction product obtained by further adding an epoxy compound to the photopolymerizable unsaturated compound according to claim 2.

4. An alkali-developable resin composition comprising a photopolymerizable unsaturated compound having a structure of a reaction product obtained by further esterifying a polybasic acid anhydride to the photopolymerizable unsaturated compound according to claim 3.

5. An alkali-developable photosensitive resin composition comprising the alkali-developable resin composition according to claim 4 and a photopolymerization initiator.

6. An alkali-developable photosensitive resin composition comprising the alkali-developable resin composition according to claim 3 and a photopolymerization initiator.

7. An alkali-developable photosensitive resin composition comprising the alkali-developable resin composition according to claim 2 and a photopolymerization initiator.

8. An alkali-developable, colored photosensitive resin composition comprising the alkali-developable photosensitive resin composition according to claim 7 and a colorant.

9. An epoxy adduct having a structure formed by adding an unsaturated monobasic acid to an epoxy compound represented by following general formula (I):

[Formula 1]

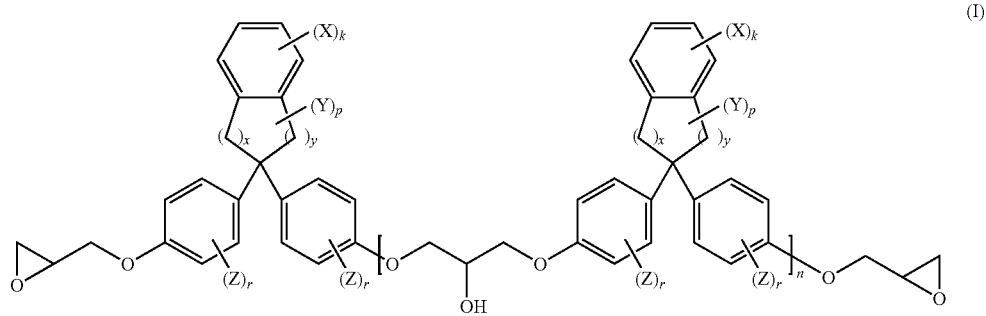

wherein,
X is selected from the group consisting of an alkyl group having 1 to 10 carbon atoms, an aryl group having 6 to 20, and a group that constitutes an aromatic ring when forming a ring with the other X;
Y and Z are each independently one of an alkyl group having 1 to 10 carbon atoms and an aryl group having 6 to 20 carbon atoms;
k, p, and r each independently are 0 to 2;
n is 0 to 10;
x is 2 or 3;
y is 0; and
an optical isomer may exists when n is not 0.

* * * * *